United States Patent
Van Heugten

(10) Patent No.: US 9,295,381 B2
(45) Date of Patent: *Mar. 29, 2016

(54) WAVEFRONT SENSOR

(71) Applicant: WaveTec Vision Systems, Inc., Aliso Viejo, CA (US)

(72) Inventor: Anthony Y. Van Heugten, Sarasota, FL (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/085,695

(22) Filed: Nov. 20, 2013

(65) Prior Publication Data

US 2014/0313487 A1    Oct. 23, 2014

Related U.S. Application Data

(63) Continuation of application No. 12/740,753, filed as application No. PCT/US2008/081584 on Oct. 29, 2008, now Pat. No. 8,619,405, which is a continuation of application No. 11/945,028, filed on Nov. 26, 2007, now Pat. No. 7,594,729.

(60) Provisional application No. 61/001,042, filed on Oct. 31, 2007.

(51) Int. Cl.
*A61B 3/10* (2006.01)
*G01J 9/00* (2006.01)
*G01M 11/02* (2006.01)

(52) U.S. Cl.
CPC .................. *A61B 3/1015* (2013.01); *G01J 9/00* (2013.01); *G01M 11/0264* (2013.01); *G01J 2009/002* (2013.01)

(58) Field of Classification Search
CPC ...................................... A61B 3/1015
USPC .......... 351/221, 205, 206, 209–213, 216, 246
See application file for complete search history.

(56) References Cited

U.S. PATENT DOCUMENTS

| | | |
|---|---|---|
| 3,947,186 A | 3/1976 | Howland |
| 4,019,813 A | 4/1977 | Cornsweet et al. |
| 4,125,320 A | 11/1978 | Rassow et al. |
| 4,172,662 A | 10/1979 | Vogel |
| 4,173,398 A | 11/1979 | Okamoto et al. |
| 4,293,198 A | 10/1981 | Kohayakawa et al. |

(Continued)

FOREIGN PATENT DOCUMENTS

| | | |
|---|---|---|
| AU | 2005234778 | 8/2011 |
| CA | 2 521 845 | 11/2004 |

(Continued)

OTHER PUBLICATIONS

Office Action mailed Jul. 25, 2008 in Chinese Patent Application No. 2004-80003472.7 filed Jan. 20, 2004.

(Continued)

*Primary Examiner* — Hung Dang
(74) *Attorney, Agent, or Firm* — Baker Botts L.L.P.

(57) ABSTRACT

The present invention relates to a wavefront sensor using a pair of screens, each having a two-dimensional array of circular apertures, to achieve Moiré effects, and its use to measure the slope of a wavefront.

20 Claims, 36 Drawing Sheets

(56) References Cited

U.S. PATENT DOCUMENTS

| | | | |
|---|---|---|---|
| 4,353,625 | A | 10/1982 | Nohda et al. |
| 4,372,655 | A | 2/1983 | Matsumura et al. |
| 4,376,573 | A | 3/1983 | Matsumura et al. |
| 4,390,255 | A | 6/1983 | Nohda et al. |
| 4,421,391 | A | 12/1983 | Matsumura et al. |
| 4,459,027 | A | 7/1984 | Kafri et al. |
| 4,541,697 | A | 9/1985 | Ramijan |
| 4,640,596 | A | 2/1987 | Humphrey |
| 4,650,301 | A | 3/1987 | Humphrey |
| 4,669,835 | A | 6/1987 | Humphrey |
| 4,692,003 | A | 9/1987 | Adachi et al. |
| 4,710,193 | A | 12/1987 | Volk |
| 4,721,379 | A | 1/1988 | L'Esperance |
| 4,730,917 | A | 3/1988 | Krueger |
| 4,911,711 | A | 3/1990 | Telfair et al. |
| 4,964,715 | A | 10/1990 | Richards |
| 4,984,883 | A | 1/1991 | Winocur |
| 4,995,716 | A | 2/1991 | Warnicki et al. |
| 5,080,477 | A | 1/1992 | Adachi |
| 5,144,478 | A | 9/1992 | Toshimitsu |
| 5,157,427 | A | 10/1992 | Humphrey |
| 5,164,750 | A | 11/1992 | Adachi |
| 5,202,708 | A | 4/1993 | Sasaki et al. |
| 5,206,672 | A | 4/1993 | Rowe |
| 5,208,619 | A | 5/1993 | Campbell |
| 5,223,863 | A | 6/1993 | Heine |
| 5,252,999 | A | 10/1993 | Sukigara |
| 5,258,791 | A | 11/1993 | Penny et al. |
| 5,270,749 | A | 12/1993 | Okamura |
| 5,282,852 | A | 2/1994 | Capetan et al. |
| 5,294,971 | A | 3/1994 | Braunecker et al. |
| 5,307,097 | A | 4/1994 | Baker |
| 5,329,322 | A | 7/1994 | Yancey |
| 5,374,193 | A | 12/1994 | Trachtman |
| 5,450,143 | A | 9/1995 | Rowe et al. |
| 5,455,645 | A | 10/1995 | Berger et al. |
| 5,493,109 | A | 2/1996 | Wei et al. |
| 5,576,780 | A | 11/1996 | Yancey |
| 5,777,719 | A | 7/1998 | Williams et al. |
| 5,796,463 | A | 8/1998 | Bullimore |
| 5,800,533 | A | 9/1998 | Eggleston et al. |
| 5,841,511 | A | 11/1998 | D'Souza et al. |
| 5,861,937 | A | 1/1999 | Fujieda |
| 5,909,268 | A | 6/1999 | Isogai et al. |
| 5,936,706 | A | 8/1999 | Takagi |
| 5,949,521 | A | 9/1999 | Williams et al. |
| 5,963,300 | A | 10/1999 | Horwitz |
| 5,968,094 | A | 10/1999 | Werblin et al. |
| 5,968,095 | A | 10/1999 | Norrby |
| 5,994,687 | A | 11/1999 | Chanteloup et al. |
| 6,002,484 | A | 12/1999 | Rozema et al. |
| 6,004,313 | A | 12/1999 | Shimmick et al. |
| 6,007,204 | A | 12/1999 | Fahrenkrug et al. |
| 6,042,232 | A | 3/2000 | Luce et al. |
| 6,043,885 | A | 3/2000 | Mazuet et al. |
| 6,050,687 | A | 4/2000 | Bille et al. |
| 6,086,204 | A | 7/2000 | Magnante |
| 6,095,651 | A | 8/2000 | Williams et al. |
| 6,096,077 | A | 8/2000 | Callahan et al. |
| 6,155,684 | A | 12/2000 | Bille et al. |
| 6,199,986 | B1 | 3/2001 | Williams et al. |
| 6,251,101 | B1 | 6/2001 | Glockler |
| 6,262,328 | B1 | 7/2001 | Wicks et al. |
| 6,264,328 | B1 | 7/2001 | Williams et al. |
| 6,270,221 | B1 | 8/2001 | Liang et al. |
| 6,271,915 | B1 | 8/2001 | Frey et al. |
| 6,275,718 | B1 | 8/2001 | Lempert |
| 6,299,311 | B1 | 10/2001 | Williams et al. |
| 6,299,618 | B1 | 10/2001 | Sugiura |
| 6,338,559 | B1 | 1/2002 | Williams et al. |
| 6,379,005 | B1 | 4/2002 | Williams et al. |
| 6,382,793 | B1 | 5/2002 | Lai et al. |
| 6,382,794 | B1 | 5/2002 | Lai et al. |
| 6,382,795 | B1 | 5/2002 | Lai |
| 6,394,605 | B1 | 5/2002 | Campin et al. |
| 6,409,345 | B1 | 6/2002 | Molebny et al. |
| 6,419,671 | B1 | 7/2002 | Lemberg |
| 6,439,720 | B1 | 8/2002 | Graves et al. |
| 6,460,997 | B1 | 10/2002 | Frey et al. |
| 6,497,483 | B2 | 12/2002 | Frey et al. |
| 6,508,812 | B1 | 1/2003 | Williams et al. |
| 6,511,180 | B2 | 1/2003 | Guirao et al. |
| 6,550,917 | B1 | 4/2003 | Neal et al. |
| 6,561,648 | B2 | 5/2003 | Thomas |
| 6,570,143 | B1 | 5/2003 | Neil et al. |
| 6,572,230 | B2 | 6/2003 | Levine |
| 6,575,572 | B2 | 6/2003 | Lai et al. |
| 6,578,963 | B2 | 6/2003 | Pettit |
| 6,585,723 | B1 | 7/2003 | Sumiya |
| 6,588,902 | B2 | 7/2003 | Isogai |
| 6,598,975 | B2 | 7/2003 | Liang et al. |
| 6,601,956 | B1 | 8/2003 | Jean et al. |
| 6,609,793 | B2 | 8/2003 | Norrby et al. |
| 6,609,794 | B2 | 8/2003 | Levine |
| 6,626,535 | B2 | 9/2003 | Altmann |
| 6,626,538 | B1 | 9/2003 | Arrowsmith |
| 6,634,751 | B2 | 10/2003 | Turner et al. |
| 6,637,884 | B2 | 10/2003 | Martino |
| 6,658,282 | B1 | 12/2003 | Eagan et al. |
| 6,679,606 | B2 | 1/2004 | Campin et al. |
| 6,685,319 | B2 | 2/2004 | Watson et al. |
| 6,702,806 | B2 | 3/2004 | Gray et al. |
| 6,705,729 | B2 | 3/2004 | Piers et al. |
| 6,724,464 | B2 | 4/2004 | Yang et al. |
| 6,736,509 | B2 | 5/2004 | Martino et al. |
| 6,736,510 | B1 | 5/2004 | Van Heugten |
| 6,739,721 | B2 | 5/2004 | Altmann |
| 6,761,454 | B2 | 7/2004 | Lai et al. |
| 6,781,681 | B2 | 8/2004 | Horwitz |
| 6,786,603 | B2 | 9/2004 | Altmann |
| 6,793,654 | B2 | 9/2004 | Lemberg |
| 6,819,413 | B2 | 11/2004 | Neal et al. |
| 6,827,444 | B2 | 12/2004 | Williams et al. |
| 6,836,374 | B2 | 12/2004 | Esch et al. |
| 6,905,641 | B2 | 6/2005 | Platt et al. |
| 6,908,196 | B2 | 6/2005 | Herekar et al. |
| 6,926,710 | B2 | 8/2005 | Cox et al. |
| 6,948,818 | B2 | 9/2005 | Williams et al. |
| 6,997,555 | B2 | 2/2006 | Dick et al. |
| 7,018,376 | B2 | 3/2006 | Webb |
| 7,034,949 | B2 | 4/2006 | Horwitz |
| 7,044,602 | B2 | 5/2006 | Chernyak |
| 7,044,604 | B1 | 5/2006 | Arrowsmith |
| 7,057,806 | B2 | 6/2006 | Atkinson |
| 7,066,928 | B2 | 6/2006 | Dick et al. |
| 7,068,439 | B2 | 6/2006 | Esch et al. |
| 7,070,276 | B2 | 7/2006 | Koretz |
| 7,077,522 | B2 | 7/2006 | Williams |
| 7,111,938 | B2 | 9/2006 | Andino et al. |
| 7,182,780 | B2 | 2/2007 | Terwee et al. |
| 7,237,898 | B1 | 7/2007 | Hohla et al. |
| 7,255,442 | B2 | 8/2007 | Bucourt et al. |
| 7,303,281 | B2 | 12/2007 | Wakil et al. |
| 7,336,371 | B1 | 2/2008 | Haidner et al. |
| 7,341,348 | B2 | 3/2008 | Eagan |
| 7,350,916 | B2 | 4/2008 | Hong et al. |
| 7,350,920 | B2 | 4/2008 | Levine |
| 7,357,509 | B2 | 4/2008 | Williams et al. |
| 7,374,286 | B2 | 5/2008 | Fujieda et al. |
| 7,377,641 | B2 | 5/2008 | Piers et al. |
| 7,380,942 | B2 | 6/2008 | Molebny et al. |
| 7,401,919 | B2 | 7/2008 | Vogelsang et al. |
| 7,406,263 | B2 | 7/2008 | Graves et al. |
| 7,416,305 | B2 | 8/2008 | Williams et al. |
| 7,425,067 | B2 | 9/2008 | Warden et al. |
| 7,441,901 | B2 | 10/2008 | Liang |
| 7,445,335 | B2 | 11/2008 | Su et al. |
| 7,448,752 | B2 | 11/2008 | Levine |
| 7,455,407 | B2 | 11/2008 | Neal et al. |
| 7,461,938 | B2 | 12/2008 | Lai |
| 7,467,869 | B2 | 12/2008 | Kahlen |
| 7,475,989 | B2 | 1/2009 | Campbell et al. |
| 7,476,248 | B2 | 1/2009 | Harris et al. |
| 7,478,908 | B2 | 1/2009 | Lai et al. |

(56) References Cited

U.S. PATENT DOCUMENTS

| | | |
|---|---|---|
| 7,490,938 B2 | 2/2009 | Latkany |
| 7,490,940 B2 | 2/2009 | Lai et al. |
| 7,517,087 B2 | 4/2009 | Dick et al. |
| 7,543,937 B2 | 6/2009 | Piers et al. |
| 7,556,378 B1 | 7/2009 | Ianchulev |
| 7,594,729 B2 * | 9/2009 | Van Heugten ............... 351/221 |
| 7,845,798 B2 | 12/2010 | Kuebler |
| 7,850,308 B2 | 12/2010 | Rombach |
| 7,878,655 B2 | 2/2011 | Salvati et al. |
| 7,883,505 B2 | 2/2011 | Van Heugten et al. |
| 7,887,184 B2 | 2/2011 | Baer et al. |
| 7,988,291 B2 | 8/2011 | Ianchulev |
| 8,002,410 B2 | 8/2011 | Shea |
| 8,313,196 B2 | 11/2012 | Ianchulev |
| 8,333,474 B2 | 12/2012 | Michaels et al. |
| 8,394,083 B2 | 3/2013 | Van Heugten et al. |
| 8,475,439 B2 | 7/2013 | Van Heugten et al. |
| 8,480,659 B2 | 7/2013 | Frey et al. |
| 8,545,023 B2 | 10/2013 | Holladay et al. |
| 8,550,624 B2 | 10/2013 | Padrick et al. |
| 8,619,405 B2 * | 12/2013 | Van Heugten ............... 361/221 |
| 8,632,185 B2 | 1/2014 | Ianchulev |
| 8,764,187 B2 | 7/2014 | Padrick et al. |
| 8,876,290 B2 | 11/2014 | Sarver et al. |
| 2001/0041884 A1 | 11/2001 | Frey et al. |
| 2002/0016629 A1 | 2/2002 | Sandstedt et al. |
| 2002/0082629 A1 | 6/2002 | Cox et al. |
| 2002/0097376 A1 | 7/2002 | Applegate et al. |
| 2002/0105617 A1 | 8/2002 | Norrby et al. |
| 2002/0107567 A1 | 8/2002 | Terwee et al. |
| 2002/0118349 A1 | 8/2002 | Yang et al. |
| 2002/0133228 A1 | 9/2002 | Sarver |
| 2002/0135736 A1 | 9/2002 | Stark et al. |
| 2002/0154272 A1 | 10/2002 | Shevlin |
| 2002/0158508 A1 | 10/2002 | Watanabe |
| 2002/0163623 A1 | 11/2002 | Hirohara et al. |
| 2003/0007125 A1 | 1/2003 | Levine |
| 2003/0007127 A1 | 1/2003 | Levine |
| 2003/0009156 A1 | 1/2003 | Levine |
| 2003/0025080 A1 | 2/2003 | Sting et al. |
| 2003/0053025 A1 | 3/2003 | Turner et al. |
| 2003/0139736 A1 | 7/2003 | Sander |
| 2003/0174281 A1 | 9/2003 | Herekar et al. |
| 2003/0223037 A1 | 12/2003 | Chernyak |
| 2003/0230710 A1 | 12/2003 | Wolleschensky et al. |
| 2004/0010310 A1 | 1/2004 | Peyman |
| 2004/0054358 A1 | 3/2004 | Cox et al. |
| 2004/0088050 A1 | 5/2004 | Norrby et al. |
| 2004/0156014 A1 | 8/2004 | Piers et al. |
| 2004/0167622 A1 | 8/2004 | Sunalp et al. |
| 2004/0176753 A1 | 9/2004 | Dick et al. |
| 2004/0189938 A1 | 9/2004 | Eagan |
| 2004/0223214 A1 | 11/2004 | Atkinson |
| 2004/0263785 A1 | 12/2004 | Chernyak |
| 2005/0007603 A1 | 1/2005 | Arieli |
| 2005/0068497 A1 | 3/2005 | Hanebuchi et al. |
| 2005/0105044 A1 | 5/2005 | Warden et al. |
| 2005/0110946 A1 | 5/2005 | Youssefi et al. |
| 2005/0110949 A1 | 5/2005 | Goldfain et al. |
| 2005/0117117 A1 | 6/2005 | Bourla |
| 2005/0195360 A1 | 9/2005 | Akita et al. |
| 2005/0203422 A1 | 9/2005 | Wei |
| 2005/0225725 A1 | 10/2005 | Warden et al. |
| 2005/0241653 A1 | 11/2005 | Van Heugten |
| 2005/0243276 A1 | 11/2005 | Van Heugten et al. |
| 2005/0251115 A1 | 11/2005 | Cox et al. |
| 2005/0278004 A1 | 12/2005 | Steinert et al. |
| 2006/0007395 A1 | 1/2006 | Mayo et al. |
| 2006/0007397 A1 | 1/2006 | Lai |
| 2006/0084956 A1 | 4/2006 | Sumiya |
| 2006/0126018 A1 | 6/2006 | Liang |
| 2006/0126019 A1 | 6/2006 | Liang et al. |
| 2006/0135952 A1 | 6/2006 | Curatu et al. |
| 2006/0174281 A1 | 8/2006 | Park |
| 2006/0203196 A1 | 9/2006 | Van Heugten |
| 2006/0203198 A1 | 9/2006 | Liang |
| 2006/0232744 A1 | 10/2006 | Liang |
| 2006/0247659 A1 | 11/2006 | Moeller et al. |
| 2006/0279699 A1 | 12/2006 | Liang |
| 2007/0024808 A1 | 2/2007 | Campin et al. |
| 2007/0027442 A1 | 2/2007 | Campin et al. |
| 2007/0070292 A1 | 3/2007 | Liang |
| 2007/0070293 A1 | 3/2007 | Isogai |
| 2007/0083261 A1 | 4/2007 | Colvard |
| 2007/0115432 A1 | 5/2007 | Thibos |
| 2007/0236702 A1 | 10/2007 | Neal et al. |
| 2007/0260157 A1 | 11/2007 | Norrby |
| 2008/0004610 A1 | 1/2008 | Miller et al. |
| 2008/0033546 A1 | 2/2008 | Liang |
| 2008/0084541 A1 | 4/2008 | Lai et al. |
| 2008/0088795 A1 | 4/2008 | Goldstein et al. |
| 2008/0159642 A1 | 7/2008 | Lyuboshenko |
| 2008/0231809 A1 | 9/2008 | Haigis |
| 2008/0278683 A1 | 11/2008 | Su et al. |
| 2008/0281304 A1 | 11/2008 | Campbell |
| 2008/0291396 A1 | 11/2008 | Baer et al. |
| 2009/0002628 A1 | 1/2009 | Williams et al. |
| 2009/0002631 A1 | 1/2009 | Campbell et al. |
| 2009/0009717 A1 | 1/2009 | Barrett et al. |
| 2009/0036980 A1 | 2/2009 | Norrby et al. |
| 2009/0048608 A1 | 2/2009 | Boukhny et al. |
| 2009/0096987 A1 | 4/2009 | Lai et al. |
| 2009/0103050 A1 | 4/2009 | Michaels |
| 2009/0109401 A1 | 4/2009 | Van Heugten |
| 2009/0164007 A1 | 6/2009 | Van Heugten |
| 2010/0030225 A1 | 2/2010 | Ianchulev |
| 2010/0036386 A1 | 2/2010 | Ianchulev |
| 2010/0042210 A1 | 2/2010 | Ianchulev |
| 2010/0152847 A1 | 6/2010 | Padrick et al. |
| 2011/0001960 A1 | 1/2011 | Van Heugten |
| 2011/0013141 A1 | 1/2011 | Holladay et al. |
| 2011/0242482 A1 | 10/2011 | Olsen |
| 2012/0147460 A1 | 6/2012 | Kubler |
| 2013/0021574 A1 | 1/2013 | Van Heugten |
| 2013/0070203 A1 | 3/2013 | Michaels |
| 2013/0335705 A1 | 12/2013 | Van Heugten et al. |
| 2014/0085604 A1 | 3/2014 | Michaels |
| 2014/0111772 A1 | 4/2014 | Ikegami |
| 2014/0132922 A1 | 5/2014 | Padrick |
| 2014/0132931 A1 | 5/2014 | Holladay |
| 2014/0249624 A1 | 9/2014 | Ianchulev |
| 2015/0092158 A1 | 4/2015 | Padrick et al. |
| 2015/0157200 A1 | 6/2015 | Sarver |

FOREIGN PATENT DOCUMENTS

| | | |
|---|---|---|
| CA | 2515010 | 5/2013 |
| CN | 2010-80040737.6 | 6/2011 |
| CN | 102497833 A | 6/2012 |
| DE | 43 10 561 A1 | 9/1994 |
| DE | 19 85 7001 A1 | 6/2000 |
| EP | 0931504 A1 | 7/1999 |
| EP | 2444021 | 4/2012 |
| EP | 2453823 | 5/2012 |
| EP | 1596710 | 1/2013 |
| EP | 1 737 372 | 8/2014 |
| EP | 2 453 822 | 8/2014 |
| EP | 2 818 130 | 12/2014 |
| EP | 2 453 823 | 5/2015 |
| GB | 1 209 451 | 10/1970 |
| IL | 138282 | 7/2004 |
| JP | 11-24434 | 5/1989 |
| JP | 9-122075 | 5/1997 |
| JP | 10-272100 | 10/1998 |
| JP | 2000-139996 | 5/2000 |
| JP | 2000-197607 | 7/2000 |
| JP | 2001-507258 A | 6/2001 |
| JP | 2001-314372 A | 11/2001 |
| JP | 2002-306418 A | 10/2002 |
| JP | 2003-509731 A | 3/2003 |
| JP | 2003-102689 A | 4/2003 |
| JP | 4972546 | 4/2012 |
| WO | WO 92/01417 | 2/1992 |
| WO | WO 96/22506 | 7/1996 |

(56) References Cited

FOREIGN PATENT DOCUMENTS

| WO | 98/27863 | 7/1998 |
|---|---|---|
| WO | WO 00/33729 | 6/2000 |
| WO | WO 01/06914 | 2/2001 |
| WO | WO 01/21061 | 3/2001 |
| WO | WO 01/26591 | 4/2001 |
| WO | WO 01/58339 | 8/2001 |
| WO | WO 02/17775 | 3/2002 |
| WO | WO 03/002047 | 1/2003 |
| WO | WO 03/039356 | 5/2003 |
| WO | WO 03/050472 | 6/2003 |
| WO | WO 03/102498 | 12/2003 |
| WO | WO 2004/093663 | 11/2004 |
| WO | WO 2005/057252 | 6/2005 |
| WO | WO 2006/081031 | 8/2006 |
| WO | 2009/086059 | 7/2009 |
| WO | WO 2014/052479 | 4/2014 |

OTHER PUBLICATIONS

Office Action mailed Nov. 5, 2008 in European Patent Application 04703599.3 filed Jan. 20, 2004.
Office Action mailed May 15, 2009 in Japanese Patent Application 2001-511810 filed Jul. 27, 1999.
Rejection Decision issued Aug. 14, 2009 in Chinese Patent Application No. 2004-80003472.7 filed Jan. 20, 2004.
Office action mailed Dec. 14, 2009 in European Patent Application 04703599.3 filed Jan. 20, 2004.
Office action mailed Dec. 18, 2009 in Japanese Patent Application 2006-502878 filed Jan. 20, 2004.
Office Action mailed Feb. 9, 2010 in Japanese Patent Application 2001-511810 filed Jul. 27, 1999.
International Search Report and Written Opinion, issued Apr. 30, 2010 in related International Patent Application No. PCT/US08/81584, filed Oct. 29, 2008.
Office Action mailed Aug. 20, 2010 in Japanese Application No. 2006-502878.
English Translation of Office Action mailed May 13, 2011 in corresponding Japanese Application No. JP 2006-502878.
Office Action issued on Jan. 17, 2012 in connection with Canadian Patent Application No. 2,515,010.
Decision of Rejection (and English Translation) issued on May 11, 2012 in corresponding Japanese Patent Application No. JP 2006-502878.
Notice of Allowance issued on Sep. 17, 2012 in corresponding Canadian Application No. CA 2,515,010.
Office Action issued on Feb. 25, 2013, in corresponding U.S. Appl. No. 12/740,753.
"IOL Power Calculations Piggyback Lens," http://doctor-hill.com/iol-main/piggyback.html, accessed on Feb. 24, 2010.
"Refractive Vergence Formula Piggyback IOL Intraocular Lens Calculations," http://doctor-hill.com/iol-mail/piggyback.html, accessed on Feb. 12, 2010.
Aramberri, "Intraocular lens power calculation after corneal infrastructure surgery: Double-K method," J Cataract Refract Surg 29:2063-2068 (Nov. 2003).
Argento et al., "Intraocular lens power calculation after refractive surgery," J Cataract Refract Surg 29:1346-1351 (Jul. 2003).
Binkhorst RD., "Intraocular lens power calculation", Int Ophthalmol Clin. 1979 Winter; 19(4):237-52. (Abstract).
Binkhorst, "Power of the Pre-Pupillary Pseudoshakos," B.J.O. 56:332-37 (1972).
Binkhorst, "The Optical Design of the Intraocular Lens Implants," Opthalmic Surg 6(3):17-31 (1975).
Brandser R., "Accuracy of IOL calculation in cataract surgery", Acta Ophthalmol Scand. Apr. 1997; 75(2):162-5 (Abstract).
Castro et al., "Tilt and decentration of intraocular lenses in vivo from Purkinje and Scheimpflug imaging: Validation study," J. Cataract Refract. Surg. 2007; 33:418-429.
Chen et al., "Analysis of intraocular lens power calculation in post-radial keratotomy eyes," J Cataract Refract Surg 29:65-? (Jan. 2003).

Colenbrander, "Calculation of the Power of an Iris-Clip Lens for Distance Vision," Br. J. Ophthal. 57:735-40(1973).
Cordonnier, M., et al., "How accurate is the hand-held refractor Retinomax(R) in measuring cycloplegic refraction: a further evaluation", Strabismus. Sep. 1998;6(3):133-142 (Abstract).
Cua et al., Intraocular lens calculations in patients with corneal scarring and irregular astigmatism, J Cataract Refract Surg 29:1352-1357 (Jul. 2003).
Donoso R., et al., "Emmetropization at cataract surgery. Looking for the best IOL power calculation formula according to the eye length", Arch Soc Esp Oftalmol. Sep. 2003;78(9):477-80 (Abstract).
El-Baha SM, et al., "Intraoperative biometry for intraocular lens (IOL) power calculation at silicone, oil removal", Eur J Ophthalmol. Aug.-Sep. 2003;13(7):622-6. (Abstract).
El-Defrawy S., et al. "Evaluation of a hand-held autorefractor in children younger than 6", J Pediatr Ophthalmol Strabismus. 1998 ~ar-Apr;35(2):107-9 (Abstract).
Feiz, et al., "Intraocular Lens Power Calculation After Laser In Situ Keratomileusis for Myopia and Hyperopia—A Standard Approach," Cornea 20(8):792-797 (2001).
Feordorov et al. "Estimation of Optical Power of the Intraocular Lens," Vestn. Onamol 80(4):27-31 (1967).
Filip M., et al. "Post-operatory biometry and refraction results estimated and refraction surprises—clinical study", Oftalmologia. 2003;56(1):11-4 (Abstract).
Gernet, "IOL Calculation According to Gernet and the GOW 70 PC Programme," Abstract from Ophthalmologe 98:873-876 (2001).
Gimbel et al., "Accuracy and Predictability of Intraocular Lens Power Calculation After Laser In Situ Keratomileusis," J Cataract Refract Surg 27:571-576 (Apr. 2001).
Gimbel et al., "Accuracy and Predictability of Intraocular Lens Power Calculation After photorefractive keratectomy," J Cataract Refract Surg 26:1147-1151 (Apr. 2000).
Gupta, et al., "*Design and use of an infrared Pupilometer for real-time pupil mapping in response to incremental illumination levels,*" 2000 Optical Society of America, Total 4 pages.
Guttman, "Aberrometer Aims to Improve Refractive, Cataract Outcomes—Investigational Device Allows Evaluation of Wide Range of Eyes", Opthamology Times, Oct. 15, 2008, accessed Feb. 23, 2010, URL http://www.modernmedicine.com/modernmedicine/Refractive+Surgery+Feature/Aberrometer-aims-to-improve-refractive-cataract-ou/Article Standard/Article/detail/559856.
Hamilton et al., "Cataract Surgery in Patients with Prior Refractive Surgery", Current Opinion in Ophthalmology 14:44-53 (2003).
Happe W. et al., "Intraoperative Skiaskopie zur Bestimmung des Brechwerts einer zu implantierenden Intraokularlinse" [Intraoperative retinoscopy for determining the refractive value of an implantable intraocular lens] Klin. Monatsbl. Augenheilkd. vol. 210, No. 4, 1997, pp. 207-212.
Harvey et al., "Reproducability and accuracy of measurements with a hand held autorefractive in children," Journal of Opthalmology 81:941-948 (1997).
Hoffer KJ, et al., "A simple lens power calculation program for the HP-67 and HP-97 Calculators", JAm Intraocul Implant Soc. Oct. 1978; 4(4):197-9. (Abstract).
Hoffer, "Calculating Corneal Power After Refractive Surgery," Cataract & Refractive Surgery Today 4(4):23-25 (Apr. 2004).
Hoffer, "Mathematics and computers in intraocular lens calculation," Am Intra-Ocular Implant Soc. J. 1(1):4-5 (1975).
Holladay, et al., "A three-part system for refining intraocular lens power calculations," J. Cataract Refract Surg. 14:17-24 (Jan. 1988).
Holladay, Jack T., "Refractive Power Calculations for Intraocular Lenses in Phakic Eye," American Journal of Ophthalmology, Jul. 1993, pp. 63-66.
Holladay, JT et al., Refining Toric Soft Contact Lens Prescriptions. Clao J. 1984, 10:326-31.
Holladay, JT, et al. "Calculating the Surgically Induced Refractive Change Following Ocular Surgery", J. Cataract Refract. Surg. 1992; 18:429-43.
Hunt et al., "Evaluation of the measurement of refractive error by the PowerRefractor: a remote, continuous and binocular measurement system of oculomotor function," Br. J. Opthalmol 87:1504-1508 (2003).

(56) References Cited

OTHER PUBLICATIONS

Ianchulev, "Method for Intraoperative Refractive IOL Calculation," Poster Presentation at Ophthalmology Conference (Apr. 2004).
Ianchulev, et al. (Aug. 2005), "Intraoperative optical refractive biometry for intraocular lens power estimation without axial length and keratometry measurements," Journal of Cataract & Refractive Surgery, vol. 31, Issue 8, pp. 1530-1536, Abstract.
Isenberg et al., "Use of the Hark Autorefractor in Children," American Journal of Ophthalmology 131(4):438-441 (2001).
Iuorno JD, et al., "Clinical comparison of the Welch Allyn SureSight handheld auto refractor versus cycloplegic auto refraction and retinoscopic refraction", J AAPOS. Apr. 2004;8(2):123-7 (Abstract).
Ivanov MN, et al., "Formula for calculating the IOL focal power", Vestn Oftalmol. Jul.-Aug. 2003;119 (4):52-4 (Abstract).
Iwami S. et al., "Prediction of Postoperative Refraction Using Intraoperative Retinoscopy" Journal of Japanese Ophthalmological Society, vol. 103, No. 7, 1999, pp. 551-555.
Koo, So, et al., "Comparison of IOL powers by corrected method in eyes after PRK and Lasik", Korean J Ophthalmol. Jun. 2002;16(1):26-31 (Abstract).
Kora et al., "Intraocular lens power calculation for lens exchange," J Cataract Surg 27:543-548 (Apr. 2001).
Liang, et al. "Comparison of the handheld Retinomax K-Plus 2 and on-table autokeratometers in children with and without cycloplegia," J Cataract Refract Surg 30:670-674 (Mar. 2004).
Liang, et al. "Aberrations and Retinal Image Quality of the Normal Human Eye", J. Optical Society of America, vol. 14, No. 11, Nov. 1997.
Liang, et al. "Comparison of Measurements of Refractive Errors Between the Hand-held Retinomax and On-table Autorefractors in Cycloplegic and Noncyclopleged Children," American Journal of Ophthalmology 136(6): 1120-1128 (Dec. 2003).
Lipatov DV., "Assessment of the efficiency of different formulae applied to calculating the optic power of an intraocular lens in transscleral fixation", Vestn Oftalmol, Nov.-Dec. 2003; 119(6):33-5 (Abstract).
Ma, et al., "Simple method for accurate alignment in toric phakic and aphakic intraocular lens implantation," J Cataract Refract Surg, Technique, Oct. 2008, vol. 34, pp. 1631-1636.
Mackool RJ., "The cataract extraction-refraction-implantation technique for IOL power calculation in difficult cases", J Cataract Refract Surg. Apr. 1998;24(4):434-5 (Abstract).
Masket, et al., "Atlas of Cataract Surgery," Book cover in 1 page, Front Matter in 11 pages (Table of Contents in 3 pages), Chapter 19 pp. 147-158, Published by Martin Dunitz Ltd 1999, United Kingdom.
Methling D, Kalb G., "A New Program for Calculating Intraocular Lenses", Klin Monatsbl Augenheilkd. Oct. 1992;201 (4):247-53 (Abstract).
Moreno-Barriuso, et al., "Laser Ray Tracing Versus Hartmann-Shack Sensor for Measuring Optical Aberrations in the Human Eye", J. Optical Society of America, vol. 17, No. 6 Jun. 2000.
Nemeth et al., "Optical and ultrasound measurement of axial length and anterior chamber depth for intraocular lens power calculation," J Cataract Refract Surg 29:85-88 (Jan. 2003).
Olsen, "Theoretical approach to intraocular lens calculation using Gaussian optics," J Cataract Refract Surg 13:141-145 (Mar. 1987).
Olsen, "Theoretical computer-assisted prediction versus SRK prediction of postoperative refraction after intraocular lens implantation," J Cataract Refract Surg 13:141-145 (Mar. 1987).
Orr et al., "Manifest Refraction Versus Autorefraction for Patients with Subfoveal Choroidal Neovascularization," Investigative Ophthalmology & Visual Science 42(2): 447-451 (Feb. 2001).
Oyo-Szerenyi et al., "Autorefraction/Autokeratometry and Subjective Refraction in Untreated and Photorefractive Keratectomy—Treated Eyes," Arch Ophthalmol, vol. 115 (Feb. 1997).
Photograph of Oculus Instrument, accessed at http://www.oculus.de/en/sites/popup_bild_gross.php?news=&id=1056 on Apr. 29, 2011.
Quiroga, et al., "*Fourier transform method for automatic processing of moire deflectograms,*" Jun. 1999, Society of Photo-Optical Instrumentation Engineers, pp. 974-982.

Raj et al., "Clinical evaluation of automated refractio in anterior chamber pseudophakia," British Journal of Ophthalmology 75:42-44 (1991).
Raj et al., "Objective autorefraction in posterior chamber pseudophakia," British Journal of Ophthalmology 74:731-733 (1990).
Raj PS, et al., "Comparative evaluation of the Allergan Humphrey 570 and Canon RK-I autorefractors: I. Objective autorefraction in normal subjects", Eye. 1992;6 (Pt 3):284-6 (Abstract).
Retzlaff J., "A new intraocular lens calculation formula", J Am Intraocul Implant Soc. Apr. 6, 1980(2):148-52. (Abstract).
Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.
Rubin A., et al., "Refractive variation during autorefraction: multivariate distribution of refractive status", Optom Vis Sci. Jun. 1995;72(6):403-10 (Abstract).
Rubin A., et al., "Variation during autorefraction: influence of two different target types", Ophthalmic Physiol Opt. Jan. 1997;17(1):38-43 (Abstract).
Sanders et al., "Comparison of the SRK/T formula and other theoretical and regression formulas," J Cataract Refract Surg. 16:341-346 (May 1990).
Sanders et al., "Comparisons of the SRK™ formula and other second generation formulas," J Cataract Refract Surg 14;136-141 (Mar. 1988).
Senjo, et al., "Prediction of Postoperative Refraction Using Intraoperative Retinoscopy," Journal of Japanese Ophthalmological Society, 1999, vol. 103, No. 7, pp. 551-555, Abstract.
Siahmed K., et al., "Optic biometry in intraocular lense calculation for cataract surgery. Comparison with usual methods", J Fr Ophtalmol. Nov. 2001;24(9):922-6 (Abstract).
Siganos et al., "Autorefractometry after laser in situ keratomileusis," J Cataract Refract Surg 29:133-137 (Jan. 2003).
Supplemental Amendment filed Apr. 1, 2010 in U.S. Appl. No. 11/110,968, filed Apr. 20, 2005.
Supplementary European Search Report for Application No. 05737636.0, Dated Mar. 19, 2009.
Steele, G., et al., "Cycloplegic auto refraction results in pre-school children using the Nikon Retinomax Plus and the Welch Allyn SureSight", Optom Vis Sci. Aug. 2003;80(8):573-7 (Abstract).
Straub et al., "*Design of a compact Shack-Hartmann aberrometr for real-time measurement of aberrations in human eyes,*" 2000 Optical Society of America, pp. 110-113.
Suto et al., "Adjusting intraocular lens power for sulcus fixation," J Cataract Refract Surg 29:1913-1917 (Oct. 2003).
Tabernero et al., "Instrument for measuring the misalignments of ocular surfaces," Optical Society of America, Oct. 30, 2006, vol. 14, No. 22.
Thall et al., "Linear Regression Software for Intraocular Lens Implant Power Calculation," American Journal of Ophthalmology 101:597-599 (May 1986).
Thijssen JM., "The emmetropic and the iseikonic implant lens: computer calculation of the refractive power and its accuracy", Ophthalmologica. 1975;171 (6):467-86 (Abstract).
Thompson et al., "A New Posterior Chamber Intraocular Lens Formula for Axial Myopes," Ophthalmology 91(5): 484-488 (May 1984).
Tromans et al., "Accuracy of intraocular lens power calculation in paediatric cataract surgery," Br J Ophthalmol 85:939-941 (2001).
Tseng, et al., "Calculating the optimal rotation of a misaligned toric intraocular lens," J Catactact Refract Surg, Laboratory Science, Oct. 2008, vol. 34, pp. 1767-1772.
Uozato et al., "Intraoperative Confirmation Device for IOL Centering," Folia Ophthalmologica Japonica, vol. 41, 1990, pp. 1325-1329.
Van Heugten, T., et al. "Validation of Novel Hartmann-Moire Wavefront Sensor with Large Dynamic Range", presented at Wavefront Congress, Feb. 17, 2008, available at http://www.wavefront-congress.org/info/listing_detail.asp?absID-12, last visited Feb. 28, 2008.

(56) References Cited

OTHER PUBLICATIONS

Villada Jr., et al., "Comparative evaluation of the Allergan Humphrey 570 and Canon RK-I autorefractors: II, Objective autorefraction in pseudophakes", Eye. 1992;6 (Pt 3):287-9 (Abstract).

Walline JJ, "Repeatability and validity of astigmatism measurements", J Refract Surg. Jan.-Feb. 1999; 15(1):23-31 (Abstract).

Wiechens, et al., "Bilateral Cataract after Phakic Posterior Chamber Top Hat-style Silicone Intraocular Lens," Journal of Refractive Surgery, Jul./Aug. 1997, vol. 13, No. 4, Cover and Table of Contents in 2 pages, pp. 392-397.

Wood IC., "A review of autorefractors", Eye. 1987;1 (Pt 4):529-35 (Abstract).

Yalvac IS, et al., "Calculation of intraocular lens power with the SRK IIformula for axial high myopia" Eur J Ophthalmol. Oct.-Dec. 1996;6(4):375-8 (Abstract).

Zaldivar et al., "Intraocular lens power calculations in patients with extreme myopia," J Cataract Refract Surg 26:668-674 (May 2000).

Office Action mailed Feb. 20, 2009 in Chinese Patent Application No. 2004-80003472.7 filed Jan. 20, 2004.

Office Action mailed in corresponding European Patent Application No. 04703 599.3 on Mar. 23, 2011.

Nanavaty, et al.: "Anterior capsule cover and axial movement of intraocular lens," Eye (2008) 22, 1015-1023.

Narvaez et al.: "Accuracy of intraocular lens power predictin using the Hoffer Q, Holladay 1, Holladay 2, and SRK/T formulas," Journal of Cataract & Refractive Surgery,Dec. 2006.

Sandstedt, et al.: "Corneal endothelial safety after ultraviolet light treatment of the light-adjustable intraocular lens," J. Cataract Refract. Surg. 2011; 37:324-327.

Dalens H., Marcellier JJ, Moussiere L., "Use of SRK (Sanders-Retzlaf-Kraft) regression formula in the preoperative calculation of the power of crystalline implants," (Abstract), 1986.

\* cited by examiner 0 degrees of rotation

WAVEFRONT SENSOR

BACKGROUND OF THE INVENTION

A wavefront sensor is a device for measuring the aberrations of an optical wavefront. Hartmann developed the Hartmann Test over one hundred years ago, yet the Hartmann class of wavefront sensors continues to be the most commonly used type of wavefront sensors to this time.

The first Hartmann Test was simply a screen, a sheet of material with a series of holes cut into it. The Hartmann screen was placed at the opening of a telescope and then viewed with the telescope's optics, either lenses or mirrors. If there was any deviation in the location of the holes of the Hartmann screen observed in the image of the Hartmann screen created by the telescope optics, then a defect was present in the telescope optics. In other words, aberrations were present in the telescope optics.

Shack modified the Hartmann test by adding a lens (also called a lenslet) into each of the holes in the Hartmann screen. The Hartmann screen with lenslets is known as the Shack-Hartmann system. Each lenslet has a controllable focal length, allowing a longer focal length than a hole without a lens could create to be introduced into the system. A hole with no lens will act as a pin-hole camera and cause a spot of light to be formed some distance downstream in the direction of the flow of light.

Liang et al. modified the Shack-Hartmann system by adapting its use to measuring the wavefront of the human eye. See U.S. Pat. No. 6,270,221.

The theory of operation when using a simple Hartmann screen as a wavefront sensor is to pass light through the Hartmann screen, then observe the location shift of the spots formed by the holes. The shift in location of the spot is a direct indicator of the angle of the light that passed through the hole, relative to the perpendicular axis. For example, if light approached and then passed through the Hartmann screen perpendicular to the flat surface of the screen (a flat wavefront), the light would form a spot at a small distance downstream to the flow of light, and the spot would appear to be in the center of the hole when viewed from the downstream side of the Hartmann screen if the observer was looking at the Hartmann screen perpendicularly. However, if the light approached the Hartmann screen at an angle, for example, if the light approached the screen such that the light's source was below the perpendicular axis of the Hartmann screen and rising up, then the points of light formed by the holes would be above the apparent center of the holes of the Hartmann screen. With the use of basic trigonometry, the distance of the lateral shift of the point of light, coupled with the distance that the point of light is away from the hole, can be used to calculate the angle of the approach of light. The spots of light form at various distances downstream from the holes, and this must be either measured or calculated in the conditions at which the light will be analyzed. These distances are known to those skilled in the art of optics.

In the case of measuring light in a manner useful to optical applications, the complex shape of the light wave must be measured. In these cases, each point of light is individually measured for movement, and the angle of light, or in other words, its slope, can be measured at each of the numerous individual locations, allowing a complex analysis to occur.

The angle (or slope) of the approaching light to be analyzed is usually very small in most optical applications. For example, with human eyes, refraction is measured in Diopters. If, for example, an eye had one Diopter of refractive error, the angle of the light to be measured from a 6 mm pupil is only one third of a degree. If light from this eye were passed through a Hartmann screen and formed a spot of light at a distance of 4 mm downstream, the spot will have shifted off-center by only 0.023 mm. Such a small shift can be difficult to detect and measure.

When lenses are added to the Hartmann screen (a Shack-Hartmann wavefront sensor), the distance between the spot of light and the screen can be increased, thereby increasing the lateral movement of the spots for any given angle of light approaching the device. This axial distance could be controlled by the focal distance of the lens. For example, if the same one Diopter light beam described in the preceding paragraph were used with typical Shack-Hartmann lenslet array with lenses having a 20 mm focal distance, the spot would shift 0.115 mm laterally (vs. 0.023 mm along a 4 mm axial distance). This increased lateral movement of 500% results in a 500% improvement to the sensitivity of the system.

However, this increase in sensitivity comes at the price of reducing the range of measurement of the device. By extending the distance that the spots of light formed away from the Hartmann screen, the Shack-Hartmann wavefront sensor causes a simultaneous increase in the variability of the shift in the axial distance that occurs along with the shift in the lateral distance, causing the spots to become no longer in the focus plane of the observing camera, which is used to detect the spot movement. With both systems, the Hartmann Screen and the Shack-Hartmann, as the spots of light shift laterally, they also shift axially, or lengthwise. For example, with a diverging wavefront passing through the system, the spots of light will all appear to be moving radially outward from each other, but they will also be moving further downstream from the holes and/or the lenses. In the case of the Hartmann Screen, the movement in both directions, laterally and axially, is less than the amount of movement caused by the Shack-Hartmann device. The axial movement of the Hartmann Screen spots is considerably less than the axial movement of the Shack-Hartmann spots, and consequently, the spots remain in focus of the observing camera throughout a higher range of measurement than the Shack-Hartmann device.

Hence, the Hartmann Screen has higher dynamic range of measurement but lower sensitivity to small light shifts, while the Shack-Hartmann system has lower dynamic range of measurement but higher sensitivity to small light shifts. Increased sensitivity comes at the expense of range, and increased range comes at the expense of sensitivity in these devices.

Many efforts have been made to overcome this deficiency in the Shack-Hartmann system. A review of the literature in the public domain will yield many examples of such efforts, but all of these efforts require that the system be made more complex with such things as moving optical parts, higher resolution, more expensive cameras, complex sub-pixel analysis, etc.

A different optical system is the Talbot wavefront sensing method (also a concept known for more than one hundred years). Talbot optics are optics made from rulings (a series of parallel lines cut into or etched onto a clear object), or cross gratings, which are two sets of parallel rulings intersecting each other at a cross angle, which cause a self-imaging pattern of lines or cross lines to form in space a predicted distance away from the Talbot optic called "shadow patterns," with the distance based upon factors such as the wavelength of light and the spacing of the ruling lines. The location of these shadow lines would move based upon the angle of light passing through the Talbot optic, but they too would move only small amounts.

To increase the movement of the shadow patterns, the Moiré effect was employed with the Talbot (or other shadow-creating) optics. U.S. Pat. No. 5,963,300 to Horwitz and U.S. Pat. No. 6,736,510 to Van Heugten describe Talbot wavefront sensing systems with the use of Moiré effects. Horwitz placed a second, identical Talbot optic behind the first Talbot optic, then rotated the second Talbot optic slightly with respect to the first Talbot optic. By doing so, the shadow pattern's movement was amplified, making the movement easier to detect. Both devices described in these patents used rulings or gratings to produce shadows and did not use Hartmann optics with circular apertures to produce light spots of concentrated, focused beams.

A moving shadow pattern (as in Talbot or Talbot Moiré) differs from the moving spots (as in the Hartmann Screen or the Shack-Hartmann device). Hartmann screens do not merely form shadows or shadow patterns, they form focused spots of light due to the holes acting as pinhole cameras, concentrating a beam diameter down to a smaller beam diameter, or a point. Shack-Hartmann devices also do not form shadow patterns; they form focused spots of light due to the lenslets refracting the light, also concentrating a beam diameter down to a smaller beam, or a point. The moving shadow patterns are not as localized and can not be measured for centration as well as the moving spots of Hartmann devices. Other advantages of moving spots versus shadows include that Hartmann-based optics can form spot patterns of light at a narrower plane from polychromatic light, whereas Talbot optics create a thicker plane which cannot be imaged by a camera as easily, if at all. This allows Hartmann-based optics to examine beams of light in multiple wavelengths if necessary, which is particularly useful when measuring the human eye, whereas Talbot based optics are limited to function in narrower wavelength bands of light. Another advantage is that in today's wavefront sensor, CCD cameras are used to view the images. CCD cameras have square pixels aligned in rows and columns, causing aliasing distortions when the shadow lines formed by Talbot optics that utilize rulings or gratings align with the rows of pixels, which interferes with the analysis. Hartmann-based optics create circular spots, which do not create this aliasing problem. Another advantage of Hartmann-based optics is that because the spots formed are circular, more efficient centroiding algorithms may be used, which cannot be used as efficiently upon the lines or squares formed by Talbot optics.

There is a need for wavefront sensors that can achieve both high sensitivity and a high dynamic range of measurement. There is also a need for wavefront sensors that result in a high image quality. There is also a need for wavefront sensors that are small, lightweight, inexpensive, versatile, and simple.

BRIEF SUMMARY OF THE INVENTION

The present invention is directed to an apparatus comprising two screens, each having a two-dimensional array of circular apertures, wherein the second screen is rotated with respect to the first screen, thereby creating a Moiré effect.

BRIEF DESCRIPTION OF THE DRAWINGS

FIG. 36A shows an emmetropic eye.

FIG. 37A shows an emmetropic eye.

FIG. 38A shows an emmetropic eye.

DETAILED DESCRIPTION OF THE INVENTION

The novel wavefront sensor described herein utilizes two screens that are rotated relative to each other to create Moiré effects to amplify the movement of the spots created by a light beam passing through a Hartmann screen. By rotating the two screens, the axial (lengthwise) distance that the spots form downstream from the screen may be reduced by design, allowing greater dynamic range of measurement. Simultaneously, the lateral movement is increased, allowing greater sensitivity to measure smaller wavefront slopes.

In one embodiment, the apparatus of the present invention comprises: a first screen comprising a first two-dimensional array of circular apertures, wherein the first screen is placed downstream of a light source; a second screen comprising a second two-dimensional array of circular apertures, wherein the second screen is placed downstream of the first screen, the second screen is in a plane parallel to the first screen, and the second screen is rotated relative to the first screen; and a light detector downstream of the second screen.

Figure 1:
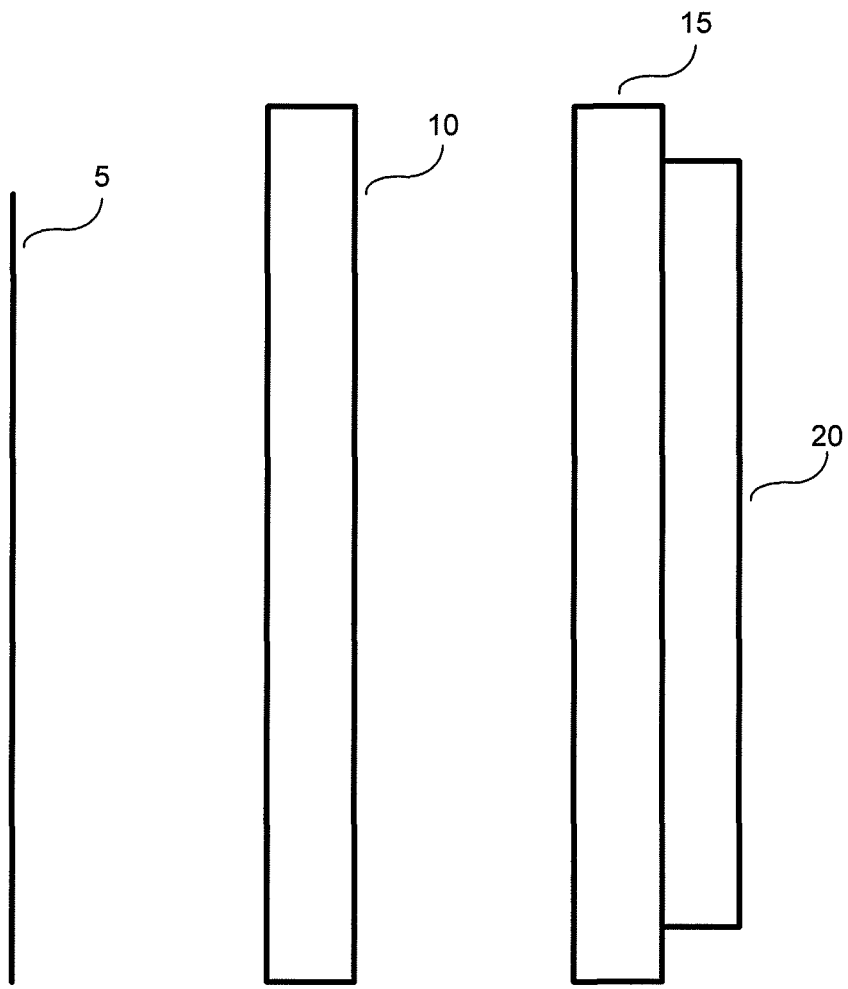
FIG. 1 shows an exemplary optical layout of the components from a side perspective.

As shown in FIG. 1, the first screen (10) is placed downstream of a light beam to be analyzed, a second screen (15) is placed downstream of the first screen, and a light detector (20) is placed downstream of the second screen. "Downstream" means further from the light beam's source on the path traveled by the light beam. In one embodiment, the light source will project a plane light wave (5) that propagates from left to right, becomes incident upon a first Hartmann screen (10), passes through the first Hartmann screen (10), becomes incident upon a second Hartmann screen (15), passes through the second Hartman screen (15), and then becomes incident upon the light detector (20). In one embodiment, the holes of the second screen (15) are on the right side of the optic in the drawing orientation of FIG. 1.

In one embodiment, the light detector (20) can convert light to electronic signals, which can be fed into a computer for analysis. Methods of feeding such data into a computer are known to those skilled in the art of Machine Vision. For example, a charge-coupled device (CCD) light detector, such as a Watec LCL 903K CCD camera, Point Grey FL2 CCD camera, or other commercially available CCD camera, can be connected to an IMperx Frame Grabber, or other commercially available frame grabber, that allows the light images to be placed into computer memory for analysis.

Figure 2:
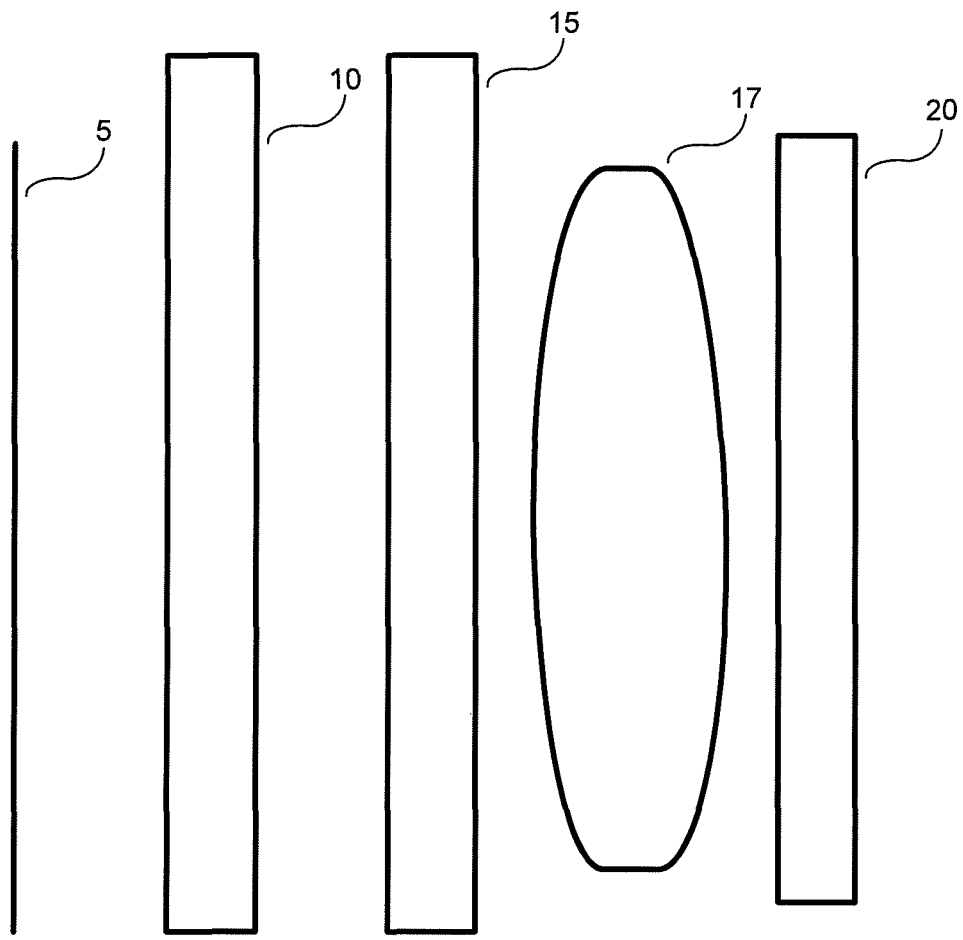
FIG. 2 shows an alternative optical layout, also from a side perspective.

FIG. 2 shows an alternative embodiment for allowing light detector (20) to accept and convert the light to electronic signals. A relay lens (17) is placed between the second screen (15) and the light detector (20), allowing the spot patterns formed by the second screen (15) to come into focus upon the light detector (20). Another position for a relay lens can be upstream of the first screen, e.g., between the light source (5) and the first screen (10). One or more lenses can be placed in one or both of these positions. Such relay optics and their design are known to those skilled in the art of optics design. An exemplary lens (17) is an Edmund Optics Triplet with a focal distance of 25 mm.

Each screen comprises a two-dimensional array of circular apertures. The two-dimensional array of circular apertures can include, for example, an array of rows and columns, but the circular apertures may be arranged in other orthogonal or non-orthogonal two-dimensional arrays. The first and second screens can have an array that is the same as, or in some cases, different from one another.

Figure 3:
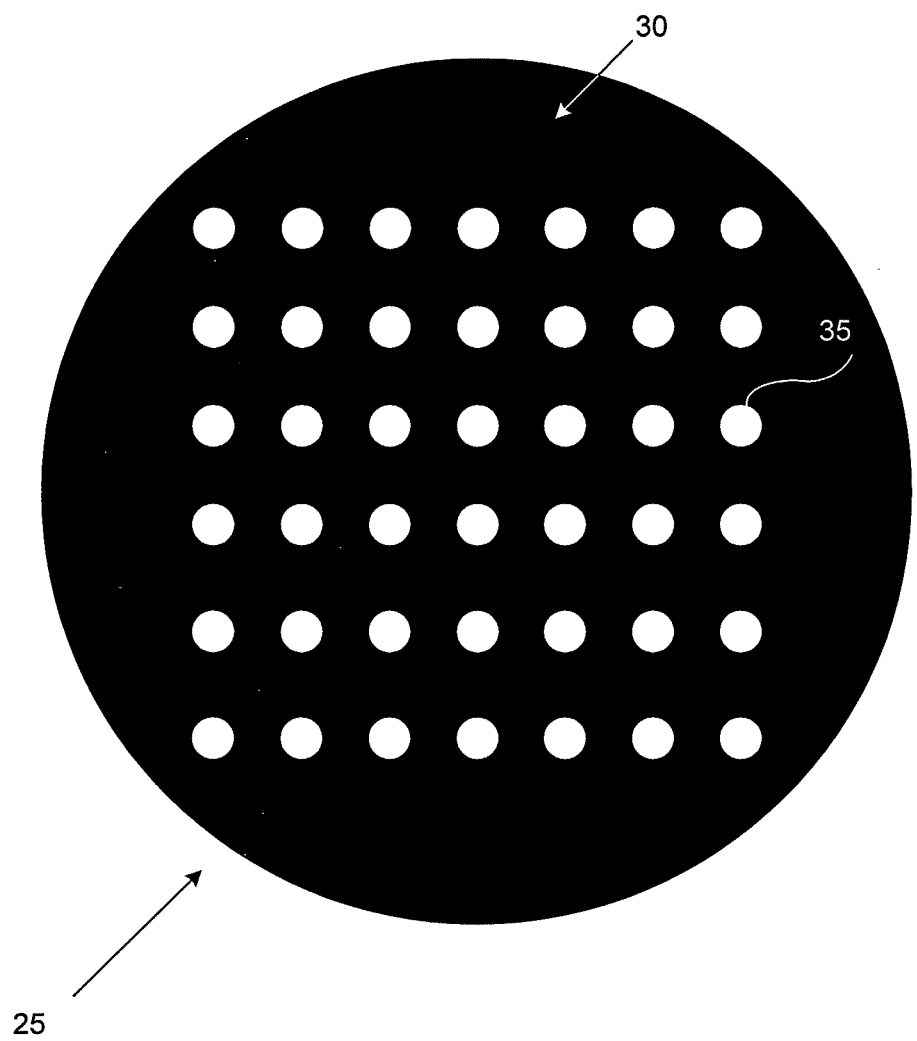
FIG. 3 shows the layout of a Hartmann screen.

Either one or both of the screens can be Hartmann screens. In one embodiment, both of the screens are Hartmann screens. FIG. 3 shows an example layout of a Hartmann screen. Clear glass substrate (25) is coated with an opaque coating (30) with multiple holes such as hole (35) made clear into the opaque coating (30). Preferably, holes such as hole (35) are arranged in a repeating array pattern with horizontal and vertical spacing, as well as hole diameter, in a consistent pattern. For example, a preferred embodiment would have holes of 0.001 inch diameter clear zone, spaced 0.002 inches apart, center to center, aligned in an orthogonal pattern. An example of substrate (25) is 0.062 inch thick Schott Glass, and an example of opaque coating (30) is chrome applied by vapor deposition.

Different holes sizes and hole spacing can be used. Preferably, each hole has a diameter of about 0.0001 inch to about 0.01 inch, about 0.0002 inch to about 0.005 inch, or about 0.001 inch. Preferably, the holes are spaced apart by about 0.0002 inch to about 0.02 inch, about 0.0004 inch to about 0.01 inch, or about 0.002 inch. The hole size and hole pattern, in addition to the degree of rotation, are selected to create a Moiré effect.

Coating thicknesses can also vary. Preferable coating thicknesses include about 0.00001 inch to about 0.01 inch, about 0.0025 inch to about 0.0075 inch, or about 0.005 inch.

One or more of the circular apertures can include a lens (lenslet). Preferably, each lenslet has the same positive focal length. In one embodiment, each circular apertures of one array comprises a lens. Such an array is called a Shack-Hartmann Lenslet Array. In another embodiment, both screens are Shack-Hartmann Lenslet Arrays.

The device can further include a beam splitter. Preferably the beam splitter is positioned upstream of the first screen, e.g., between the first screen and a light source. The beam splitter can facilitate directing the light beam, which may be particularly useful when measuring the characteristics of an eye.

Figure 4:
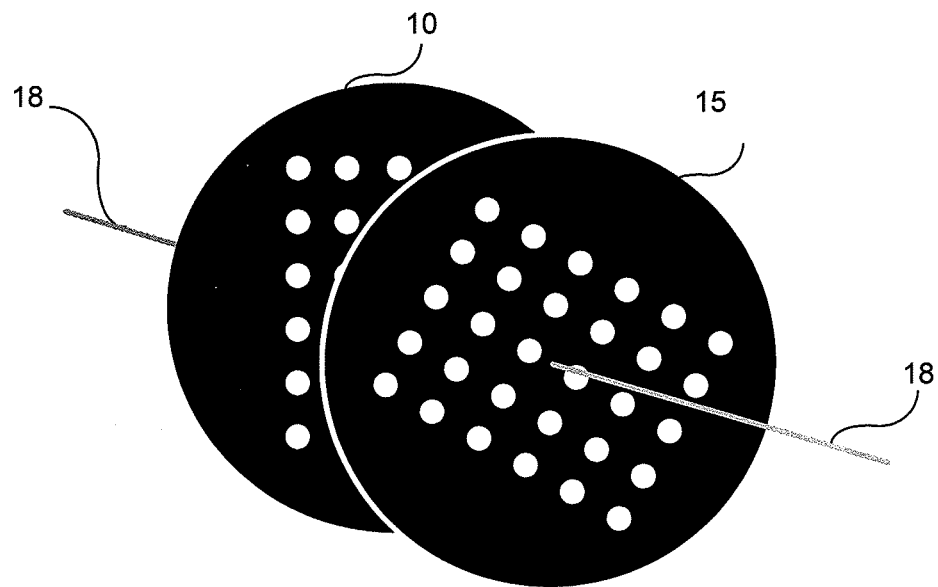
FIG. 4 shows an exemplary rotation orientation of two Hartmann screens.

FIG. 4 shows a perspective view of how the first screen (10) is oriented with respect to the second screen (15), which is a slight rotation to each other. The center of each optic would remain in the same location along the Z axis (18), and the plane of each optic would remain parallel to each other, but the orientation of rotation would occur in the remaining degree of freedom. These terms are known to those skilled in the art of optics design. Furthermore, one of ordinary skill in the art would understand that the screen rotation can also be achieved by rotating the array portion rather than rotating the entire substrate of the screen.

The degree of rotation is sufficient to create a Moiré effect and to create a detectable image of the spots. Preferably, the degree of rotation is about 1 to about 30 degrees, about 3 to about 20 degrees, about 6 to about 18 degrees, about 10 to about 14 degrees, or about 12 degrees.

The rotated screens can be achieved, for example, by the following process: lay the first screen (10) flat on a surface, then lay the second screen (15) flat upon the first screen (10) such that maximum contact surface area is achieved. With both screens still touching, rotate the second screen (15) while maintaining the same amount of contact surface. Then, introduce a distance between the screens during the assembly process, as depicted by FIG. 1.

Figure 5:
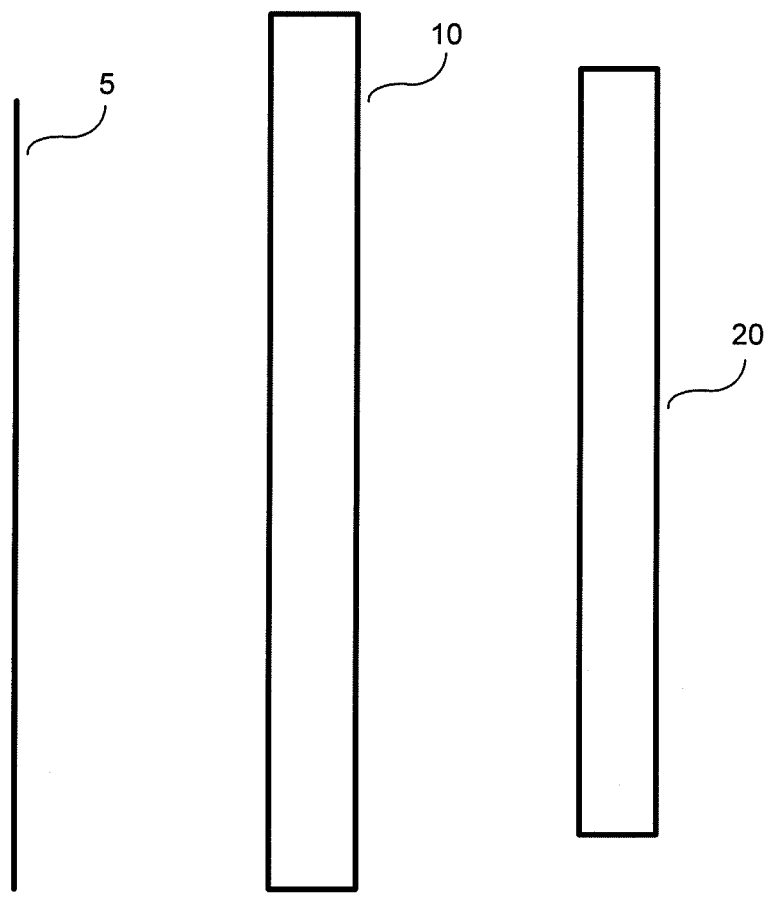
FIG. 5 shows an optical layout for determining the best distance between the two screens.

As shown in FIG. 5, to determine a gap between the first screen (10) and the second screen (15), temporarily remove the second screen (20) and replace it with light detector (20), placing light detector (20) as close as possible to first screen (10). Allow a plane wave of light perpendicular to the Z axis to pass through the first screen (10), then move light detector (20) further and closer away from the first screen (10) while observing the spots being detected by light detector (20). Select a distance between the light detector (20) and the first screen (10) at which distinct spots are being detected by light detector (20). To fine tune the setup, replace plane wave (5) with light of the type and vergence that will be analyzed in the application, and repeat the above distance setting tests. Depending upon conditions, several different distances may be discovered to work well. As a general rule, longer distances provide higher sensitivity, and closer distances provide higher dynamic range of measurement. Also, one distance may provide more dynamic range in one direction of vergence or divergence measurement, while another may provide more dynamic range in the opposite direction of vergence or divergence. After a suitable distance is selected, remove the light detector (20), and replace it with the second screen (15) at the distance and location selected, as described above. Replace light detector (20) at its appropriate position described in FIG. 1 or FIG. 2.

Once assembled in this configuration, further distances and rotation angles may be tested by moving first screen (10) and second screen (15) so that the two surfaces with the etched holes are in contact with each other, and some angle between the two is selected, such as 3 degrees. Then place within the beam of light, before it is incident upon first screen (10), a lens with a 200 mm positive focal length (i.e., 5 Diopters), and observe that there is no movement of the spots. Then, slowly move the first screen (10) away from second screen (15) while placing into the beam and then removing from the beam the 200 mm positive focal length lens and observing the movement of the spots at each distance between the two screens. As first screen (10) moves further away from second screen (15), the amount of movement of the spots will increase (i.e., the system will become more sensitive to the light angle). Once a desired distance is selected, the rotation of the two screens may be adjusted. As the angle between the two screens increases, the density of the spot pattern in increases, but the amount of movement of the spots per Diopter of light angle will decrease. FIGS. 14-21 show the variation in spot pattern density under various rotations. During these various setup conditions, one can expose the setup to a range of light conditions expected to be seen during use and select the setup conditions that produces the combination of the most distinct spot patterns coupled with the amount of movement of spots per Diopter of light vergence or divergence that will best yield the required sensitivity.

Of the many possible configurations, one exemplary setup that works when analyzing light beams in the central portion of the visible spectrum (e.g., green at 532 nm) is to have first and second screens, flat surfaces parallel to each other but rotated 12 degrees to each other, each having 0.001428 inch diameter holes spaced 0.002857 inches apart, center to center, with an optical distance of 0.024 of an inch between the first and second screens, and the light detector (e.g., a camera) set up to image the plane of where the holes are on the second screen.

The image quality achieved by the Hartmann-Moiré system can advantageously surpass the image quality achieved by a Talbot-Moiré system. The amount of spot movement in the Hartmann-Moiré system is directly proportional to the refractive power being observed by the system. However, the Talbot-Moiré system requires that the second Talbot optic be placed at a specific, calculated distance away from the first Talbot optic, described by the following formula: Distance=period squared divided by the wavelength of the light. The period is the distance between the holes. In the example described in the preceding paragraph, the second Talbot optic must be placed 0.097 inch away from the first Talbot optic, and it will not function properly if it is any closer. In contrast, Hartmann screens can be placed much closer to one another and at many more locations where it will operate properly.

The distance between screens in a Hartmann-based system is not constrained by this Talbot formula, proving that it works under a different set of principles of physics. The Hartmann-Moiré system described herein will work at the same distance that the Talbot-Moiré formula prescribes, but it also works at many other distances that would not work with Talbot-Moiré system. This flexibility of distances allows measurements of a wider spectrum of light wavelength. Also, a smaller distance between screens can be used with the Hartmann-Moiré system. This can be quite useful in optical applications wherein the observer or camera must simultaneously view the image of an eye and the spot pattern. The image of the eye comes into focus at the first screen, but the spots are in focus at the second screen, which is where the camera focuses. If the distance between the two screens is too great, the eye becomes out of focus to the camera. When this distance can be made shorter, as in the present system, then the image of the eye formed at the first screen can be in better focus to the camera that is focused at the second screen, providing a compound image of both the eye and the spots, with the spots superimposed over the eye image. This allows for a more precise determination of the refractive power of the eye at each particular spot location because each spot can be associated with a particular corresponding location of the eye.

In one embodiment, the invention provides a large dynamic range of measurement and/or a high level of sensitivity to measure smaller wavefront slopes. Preferably, the invention provides both a large dynamic range of measurement and a high level of sensitivity to measure smaller wavefront slopes. In particular, the invention can be configured to provide a measurement accurate within about 0.5D, 0.4D, 0.3D, 0.25D, 0.23D, 0.2D, or 0.1D over a range of about 5D, 7D, 10D, 11D, 15D, 16D, 17D, 18D, 20D, 24D, 30D, 35D, 38D, or 40D, or other increments within these ranges.

With experimental trials, varying one or more variable at a time—optical configuration, array pattern, hole size, hole spacing, hole location, screen spacing, screen materials, screen rotation angles, light wavelength, light detector type, etc.—will produce various densities and response rates of movement of the spots, and an appropriate combination can be selected to best suit the particular application.

Figure 6:
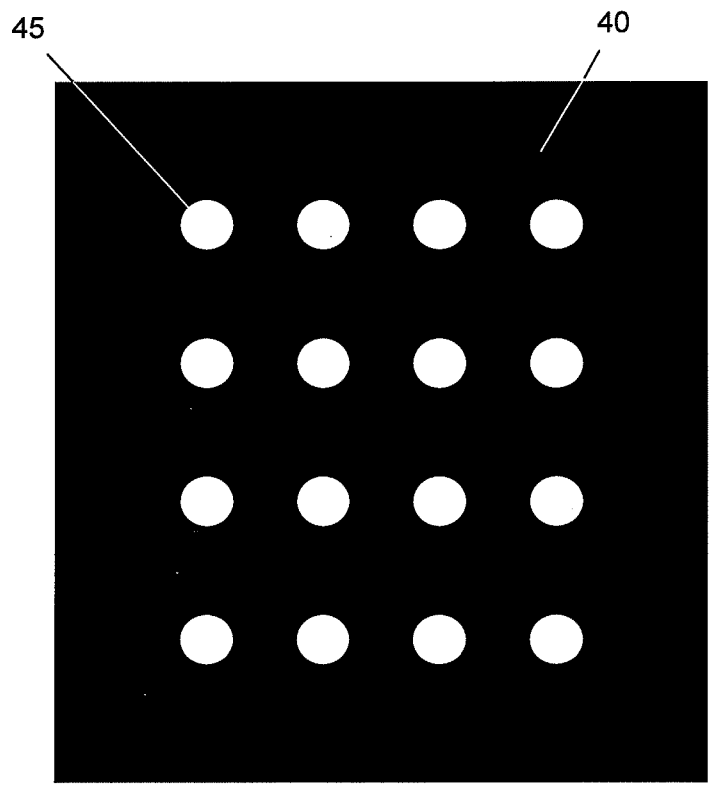
FIG. 6 shows an exemplary spot pattern created by a plane light wave passing through the layout depicted by FIG. 1.

FIG. 6 shows a field of view (40) (the image that light detector (20) produces) having an exemplary array of spots produced by a planar wave of light that passed through both screens. The distance between all of the spots increases as the relative rotation angle between the first screen and the second screen decreases in angle, and the distance decreases as the rotation increases. Example spot (45) is shown in an example location. The location of each spot is recorded with a known beam of light being examined by the entire device. Each spot of light will move in direction and magnitude in relation to the change of the slope of the light that has passed through the device in the zone being represented by that spot. In other words, if all the spots move uniformly, the entire beam of light possesses the same change in slope across it, in a uniform pattern. If some spots move more or less than others, that indicates a more or less change of slope for the area that that particular spot represents.

One of ordinary skill in the art, e.g., one familiar with Machine Vision and computer programming, knows how to instruct a computer to measure the movement of the spots. Commercially available programs such as Matlab, or other available source code for spot centering, provide such routines.

Figure 7:
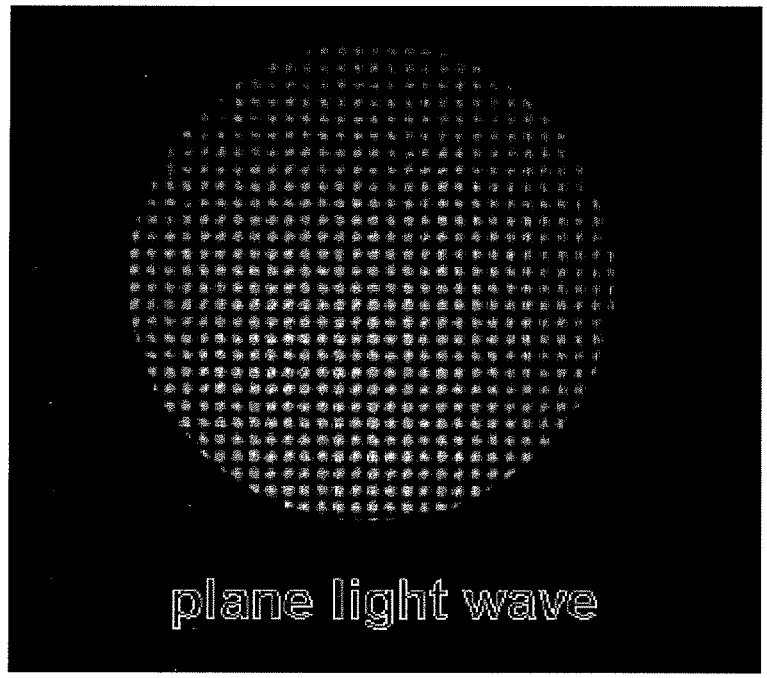
FIG. 7 shows a Point Grey FL2 CCD camera photograph of the exemplary spot pattern created by a plane light wave passing through the layout depicted by FIG. 1.
Figure 8:
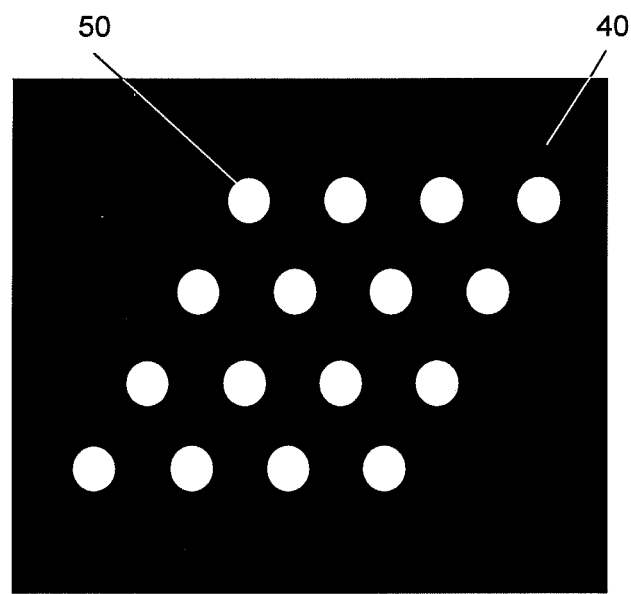
FIG. 8 shows an exemplary spot pattern created by a cylindrical light wave passing through the layout depicted by FIG. 1.
Figure 9:
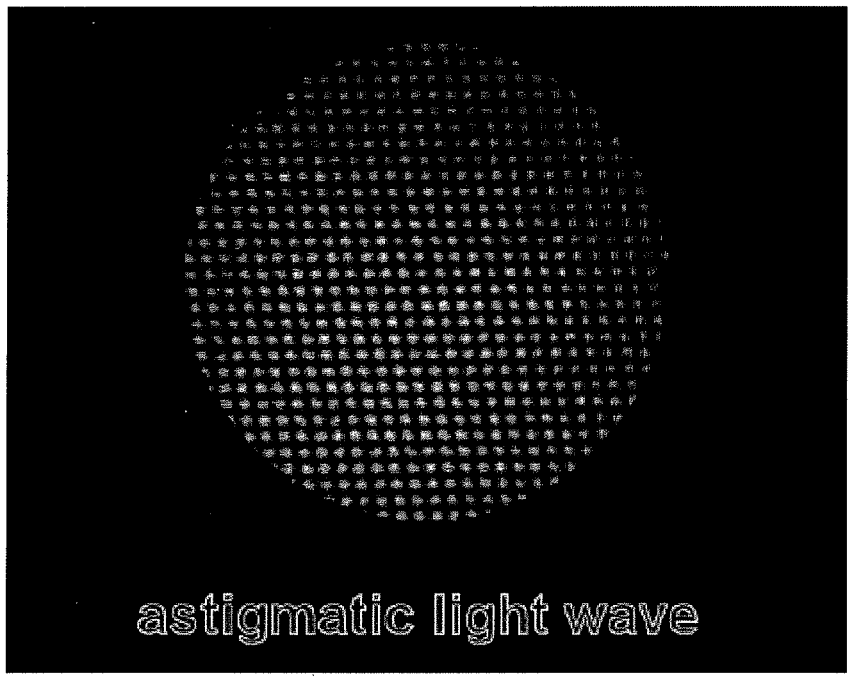
FIG. 9 shows a Point Grey FL2 CCD camera photograph of the exemplary spot pattern created by a cylindrical light wave (i.e., the beam has an astigmatism) passing through the layout depicted by FIG. 1.

If the planar light beam used in FIGS. 6 and 7 is replaced with a light beam having an astigmatism, the spot would move to a new location as shown by example spot (50) in FIGS. 8 and 9. The pattern of spots in the field of view (40) shown in FIG. 8 is an example of pure cylinder deviation, which is a term understood by those skilled in the art of optics design.

Figure 10:
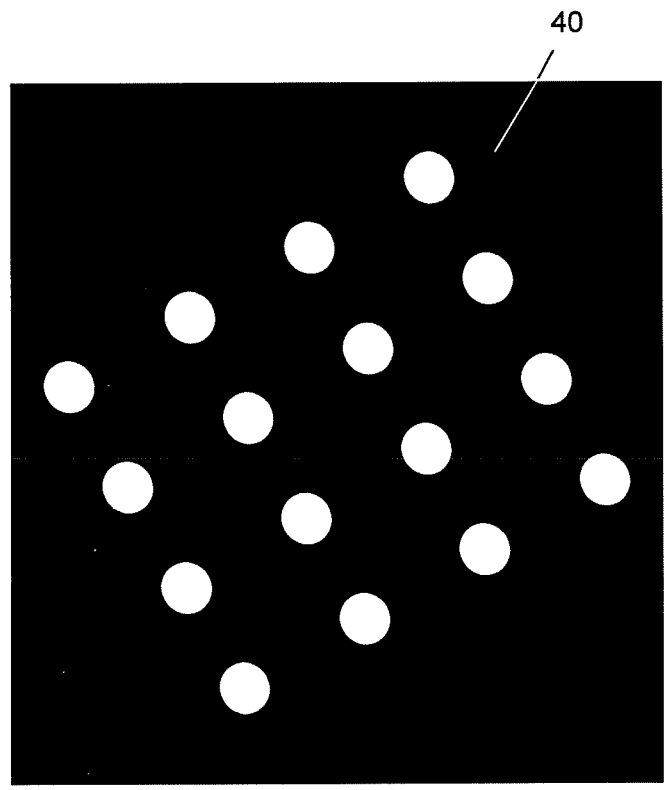
FIG. 10 shows an exemplary spot pattern created by a purely spherical light wave passing through the layout depicted by FIG. 1.
Figure 11:
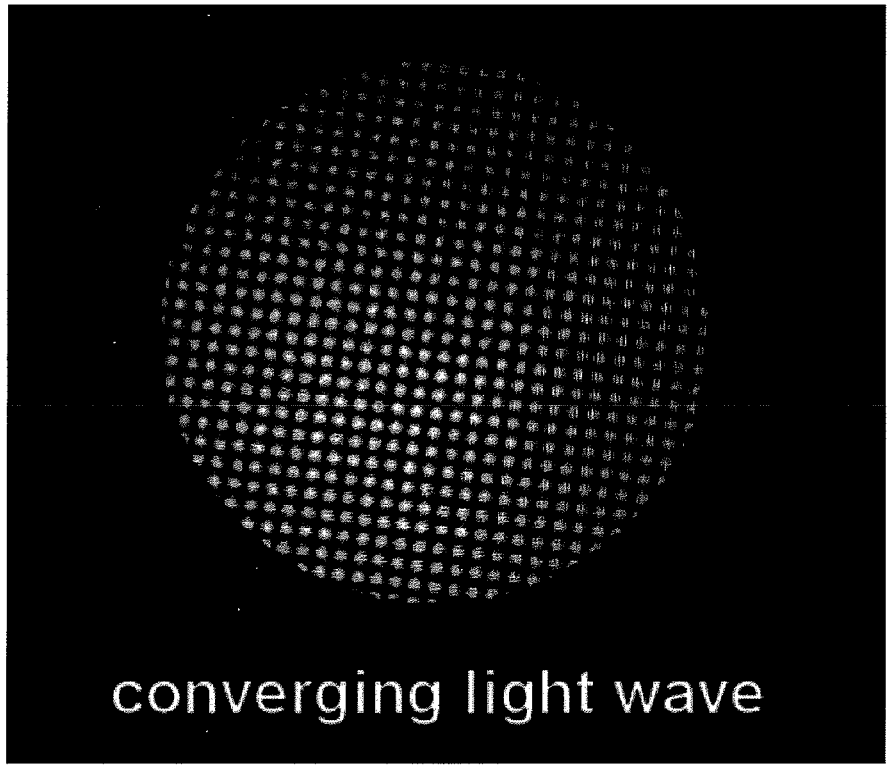
FIG. 11 shows a Point Grey FL2 CCD camera photograph of the exemplary spot pattern created by a converging light wave passing through the layout depicted by FIG. 1.
Figure 12:
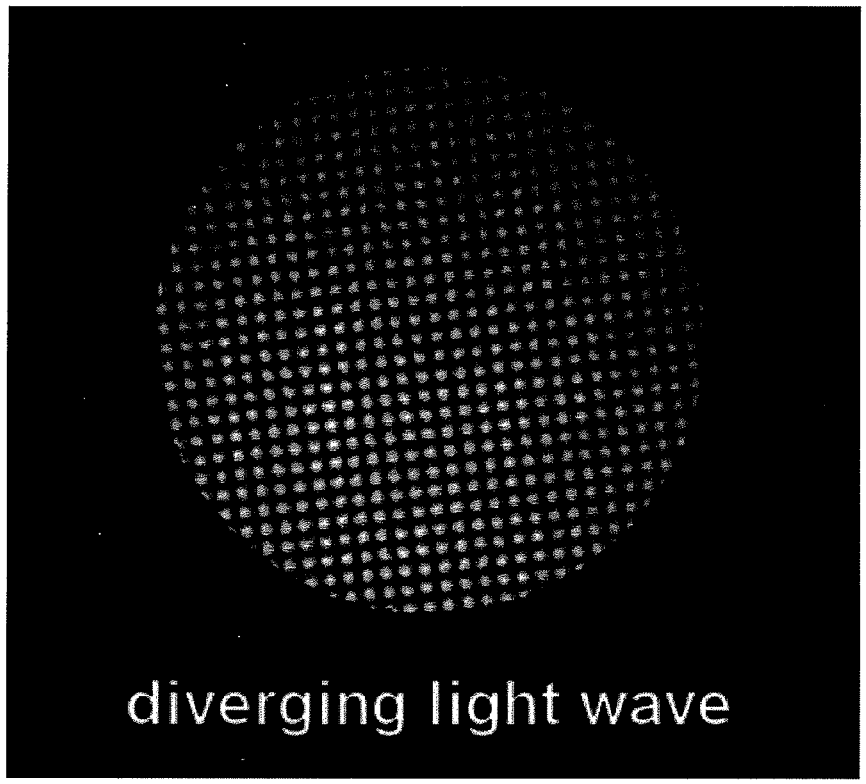
FIG. 12 shows a Point Grey FL2 CCD camera photograph of the exemplary spot pattern created by a diverging light wave passing through the layout depicted by FIG. 1.

If the planar light beam used in FIGS. 6 and 7 is replaced with a light beam having a purely spherical change to its slope, the exemplary spot pattern would appear as in FIGS. 10-12.

Figure 13:
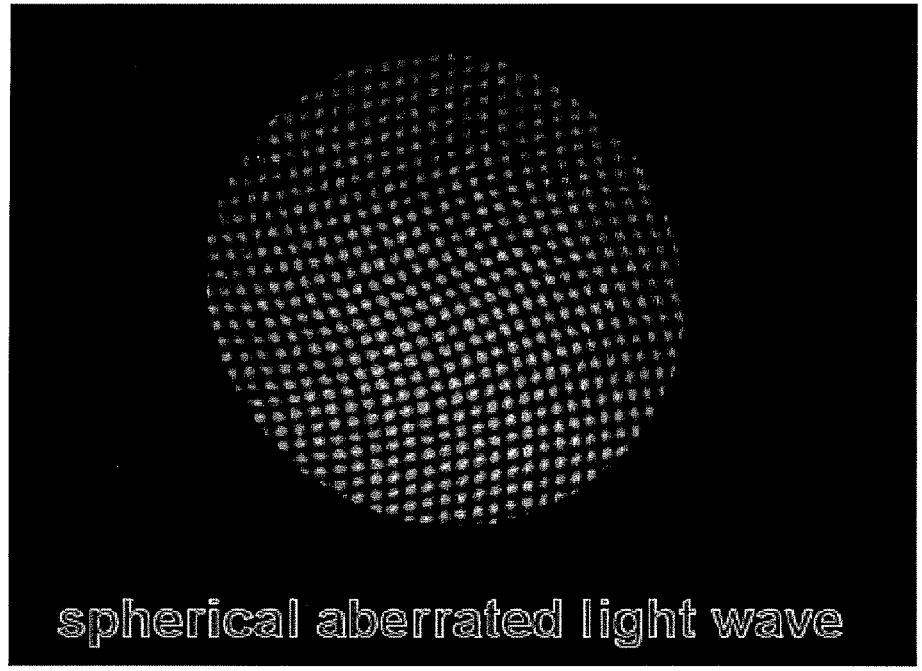
FIG. 13 shows a Point Grey FL2 CCD camera photograph of the exemplary spot pattern created by a spherical aberrated light wave passing through the layout depicted by FIG. 1.
Figure 14:
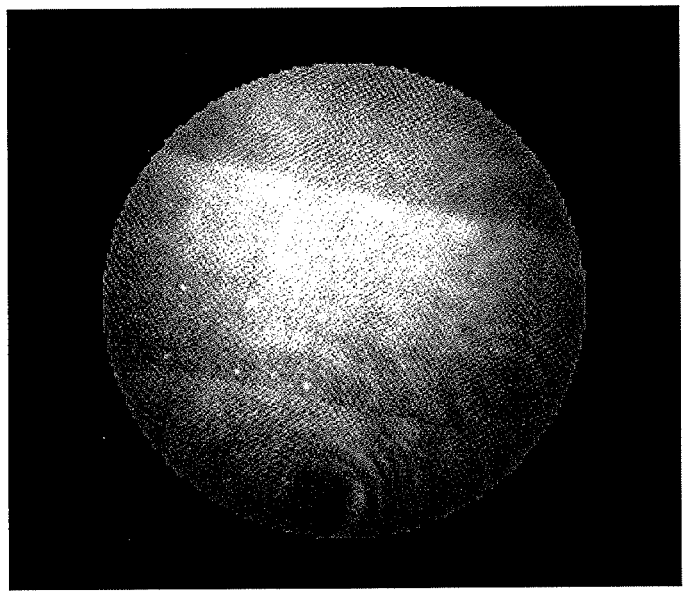
FIG. 14 shows a Point Grey FL2 CCD camera photograph of the image formed when two Hartmann screens are positioned at zero degrees rotation.
Figure 15:
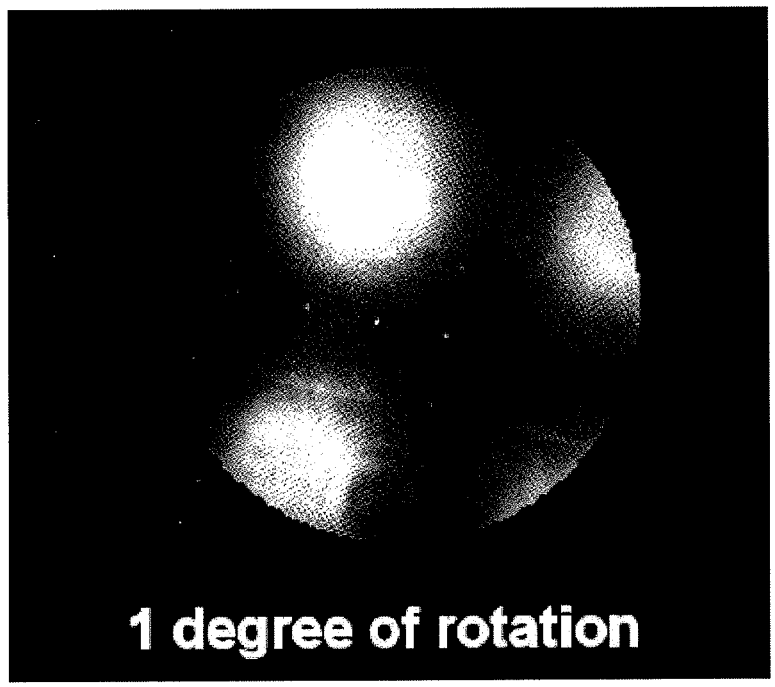
FIG. 15 shows a Point Grey FL2 CCD camera photograph of the image formed when two Hartmann screens are positioned at one degree rotation.
Figure 16:
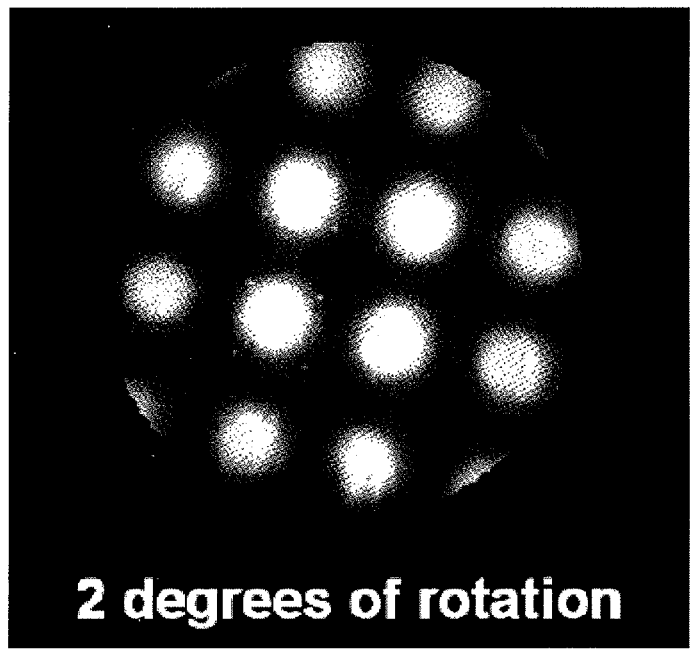
FIG. 16 shows a Point Grey FL2 CCD camera photograph of the image formed when two Hartmann screens are positioned at two degrees rotation.
Figure 17:
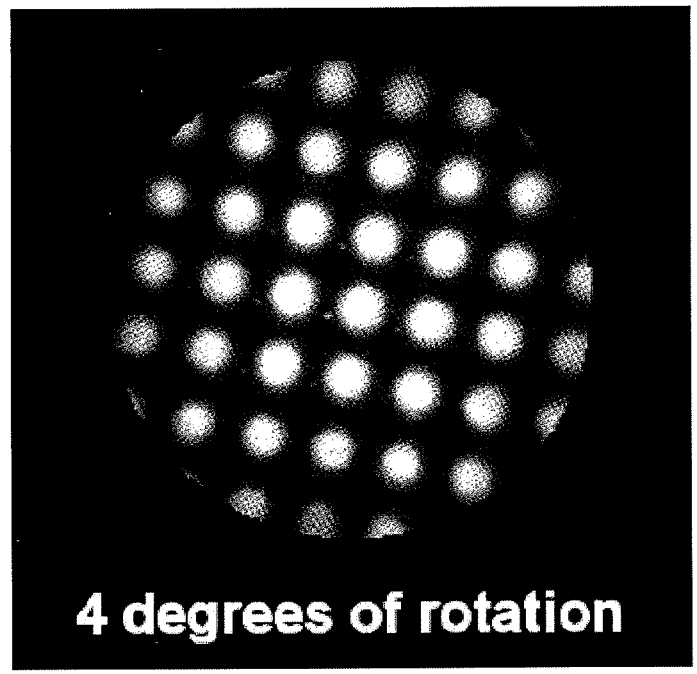
FIG. 17 shows a Point Grey FL2 CCD camera photograph of the image formed when two Hartmann screens are positioned at four degrees rotation.
Figure 18:
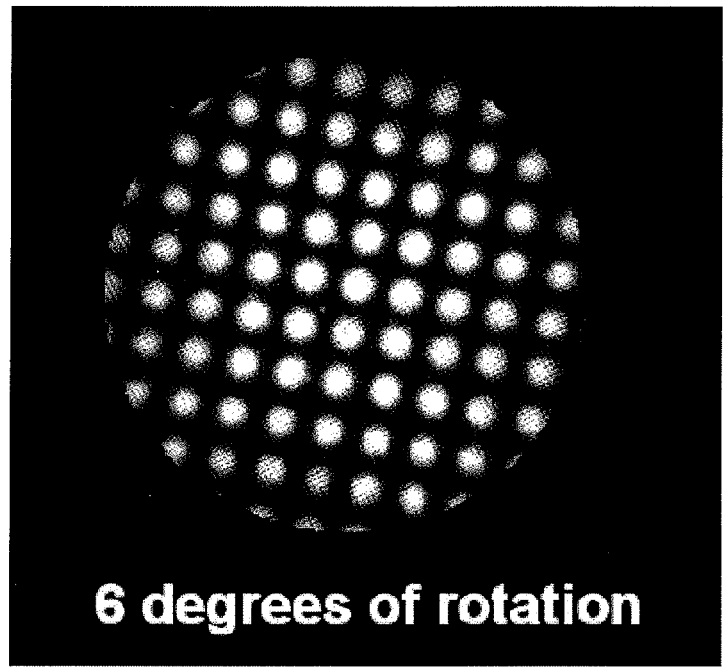
FIG. 18 shows a Point Grey FL2 CCD camera photograph of the image formed when two Hartmann screens are positioned at six degrees rotation.
Figure 19:
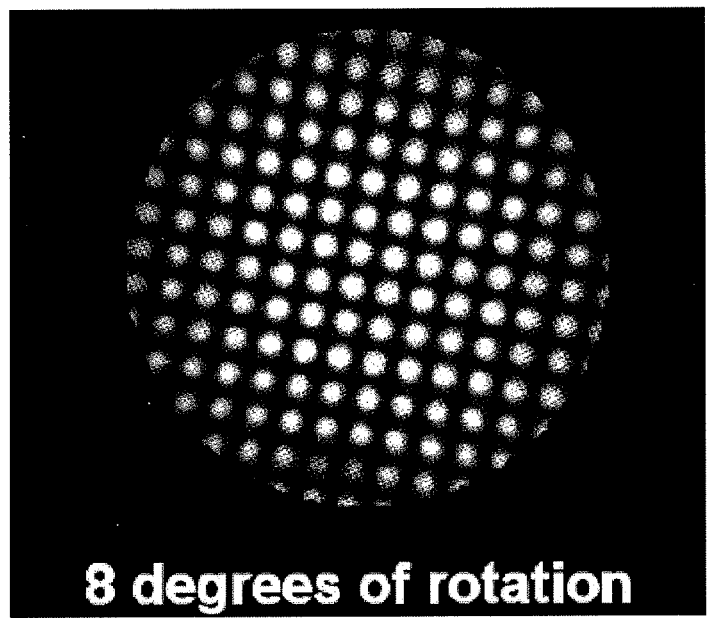
FIG. 19 shows a Point Grey FL2 CCD camera photograph of the image formed when two Hartmann screens are positioned at eight degrees rotation.
Figure 20:
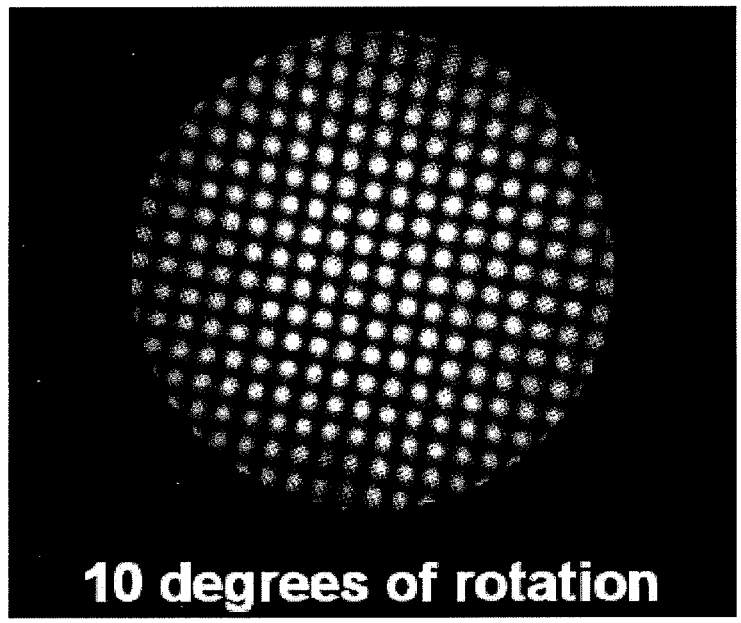
FIG. 20 shows a Point Grey FL2 CCD camera photograph of the image formed when two Hartmann screens are positioned at ten degrees rotation.
Figure 21:
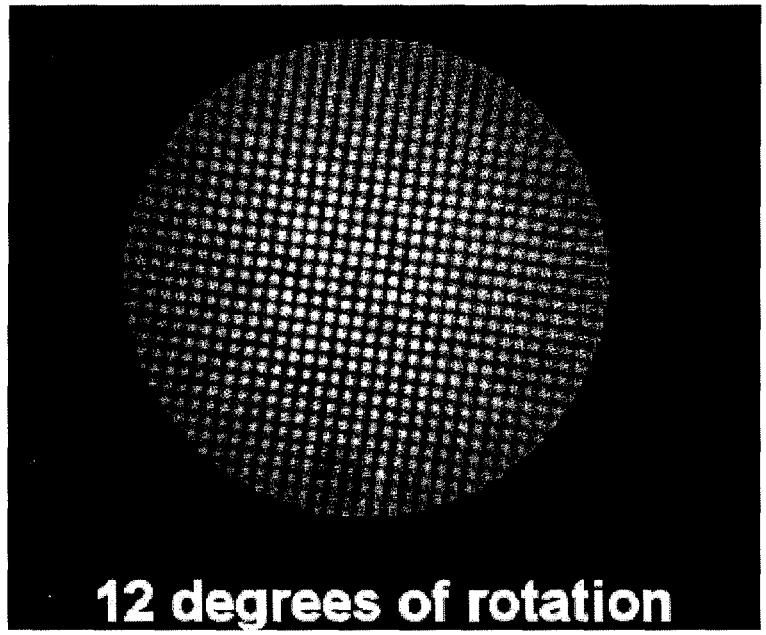
FIG. 21 shows a Point Grey FL2 CCD camera photograph of the image formed when two Hartmann screens are positioned at twelve degrees rotation.

If the planar light beam used in FIGS. 6 and 7 is replaced with a light beam having spherical aberration in its slope, the exemplary spot pattern would appear as in FIG. 13.

To calibrate the system, the preferred method is to pass a plane wave of light through the system and record the location of all the spots. Then pass a series of different light beams through the system with known amounts of sphere and cylinder changes, and record the movement of each of the spots at each location under each light beam condition. From this calibration, the relationship of the movement of the spots to the slope change of the light beam being analyzed can be quantified, then used for the computation step when the device is used in service. One of ordinary skill in the art of optics design knows how to create various optical wavefronts for this calibration method. One way to do so would be to purchase a 25 mm diameter collimated laser beam from such suppliers as Newport Optics, Melles Griot, or Thor Labs, and then purchase an Optometrists Trial Lens set from any ophthalmic or optometric supplier such as Reichert, American Optical, or other vendors, then place these trial lenses within the laser beam.

The device described above can be used to measure the slope of a wavefront. The device can be used in a variety of optical applications, such as measuring the characteristics of a lens, including an eye. A method of measuring characteristics of a lens comprises: directing light into the lens; directing the light from the lens through a first screen comprising a first two-dimensional array of circular apertures; directing the light from the first screen through a second screen comprising a second two-dimensional array of circular apertures, wherein the second screen is placed downstream of the first screen, the second screen is in a plane parallel to the first screen, and the second screen is rotated relative to the first screen; and detecting the light from the second screen at a light detector. Similarly, the device can be used to measure the characteristics of an eye by first directing light, e.g., a small diameter beam of light, into an eye. The eye reflects the beam out, and then the reflected beam is directed into the first and second two-dimensional arrays and a light detector. These methods can be used with any of the device embodiments described herein.

The present invention is further described by the following non-limiting examples.

EXAMPLE 1

Testing the Wavefront Sensor with Spherical and Cylindrical Trial Lenses

Figure 22:
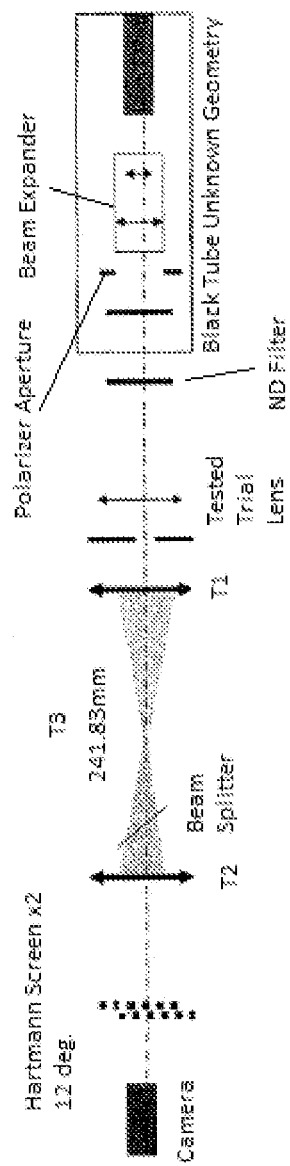
FIG. 22 show an exemplary test configuration for Topcon trial lenses.

Data were measured at a wavelength of 532 nm without focus adjustment so that the full range of wavefront vergences was presented to the wavefront sensor. The accuracy and dynamic range of the Hartmann-Moiré wavefront sensor was evaluated by measuring defocus and astigmatism induced by a series of standard Topcon spherical lenses (e.g., 77 lenses from −20D to +18D) and cylindrical trial lenses (e.g., 16 lenses from −8D to 8D). Repeatability of the Hartmann-Moiré instrument was assessed by taking 3 repeated measurements within a 2-minute period. Measured trial lens values with the Hartmann-Moiré wavefront sensor were compared to lens values verified with a standard lensometer. Analyses were based on a 4 mm pupil diameter specified in the software. The test configuration is shown in FIG. 22.

Figure 23:
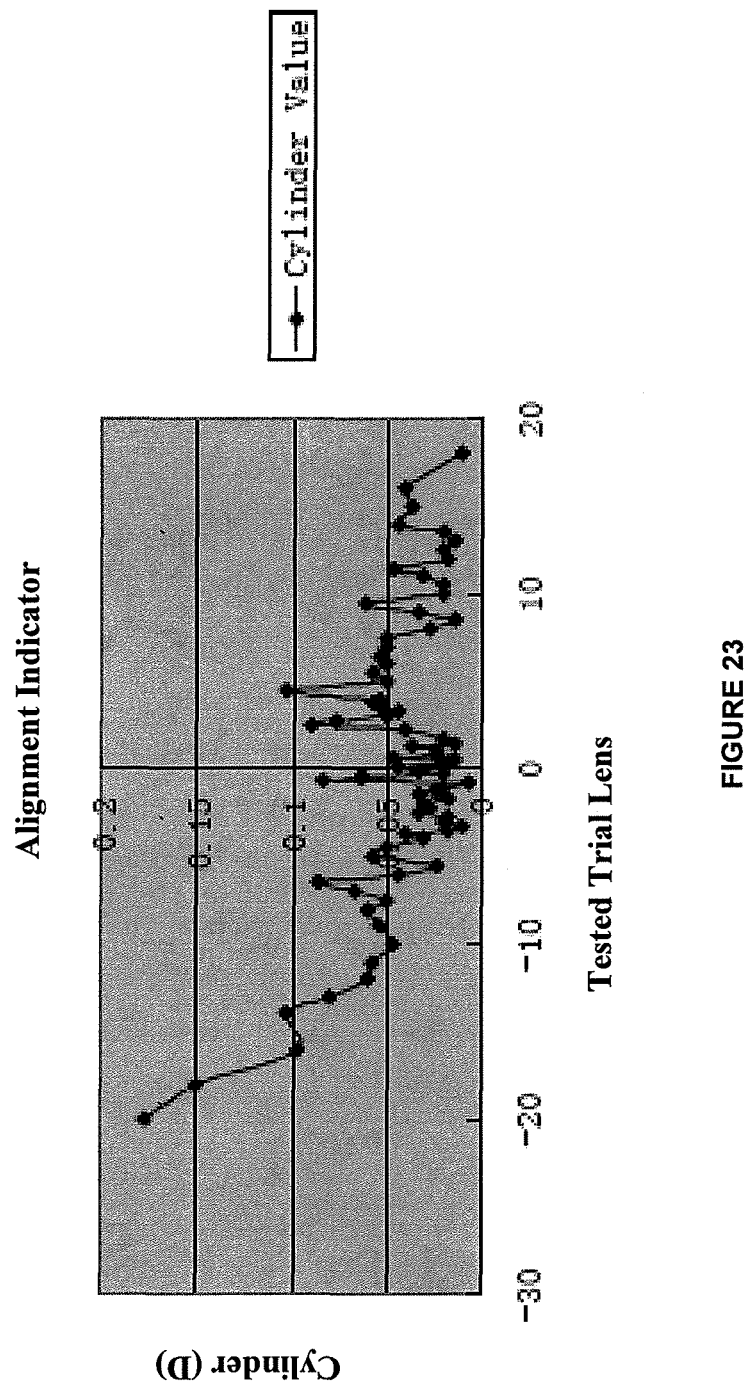
FIG. 23 shows measurements to assure tight alignment tolerance for the testing of trial lenses. The amount of measured cylinder was measured using a sphere lens from about −20D to +18D with fixed scheme.
Figure 24:
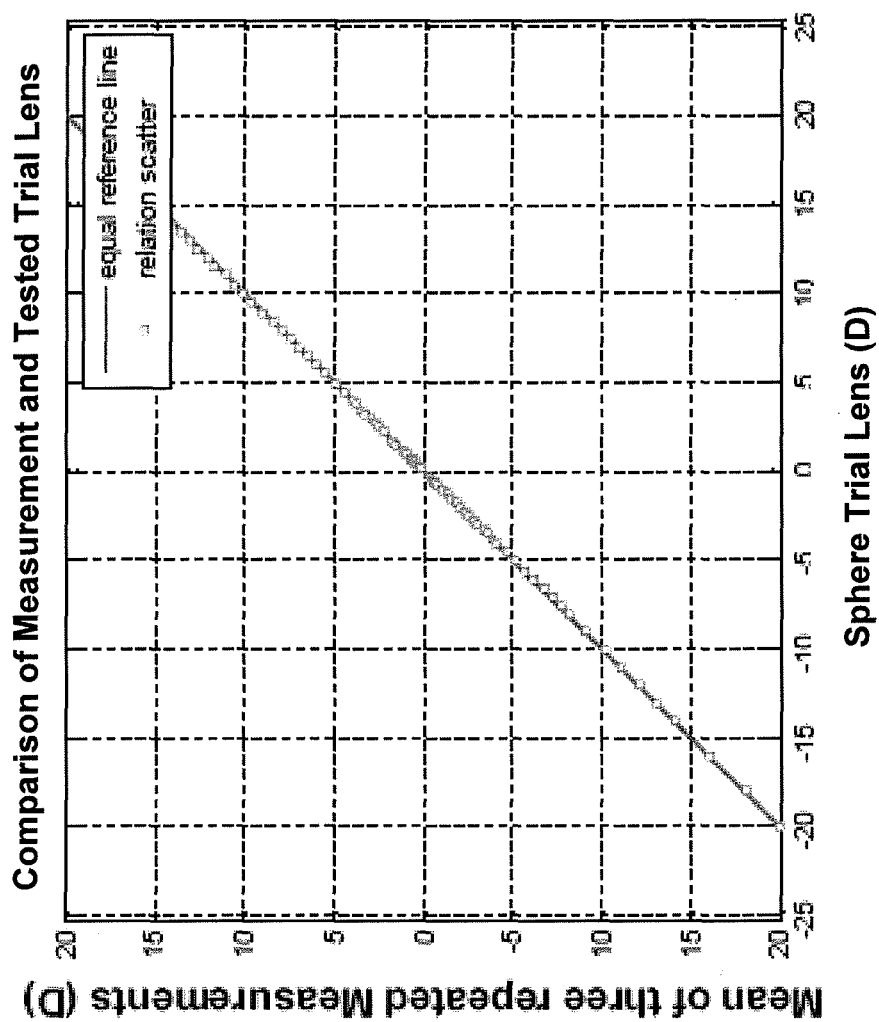
FIG. 24 shows the results of a comparison of measurement and tested trial lenses for spherical test lenses from −20D to +18D (correlation coefficient r=1.000). From −0.75D to +0.75D, the increments of the test lenses was 0.125D.
Figure 25:
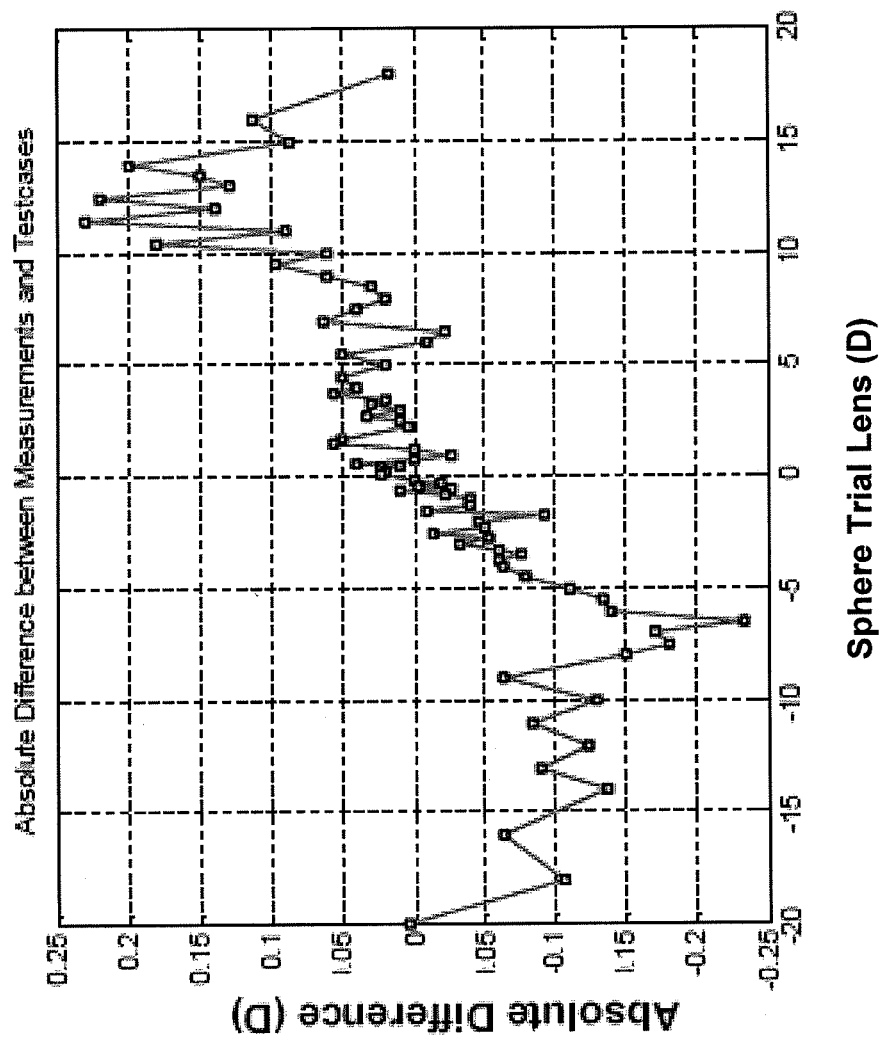
FIG. 25 shows the results of absolute difference between measurements and test lenses for spherical test lenses from −20D to +18D (Absolute mean difference: 0.0682D, Maximum difference: 0.23D).
Figure 26:
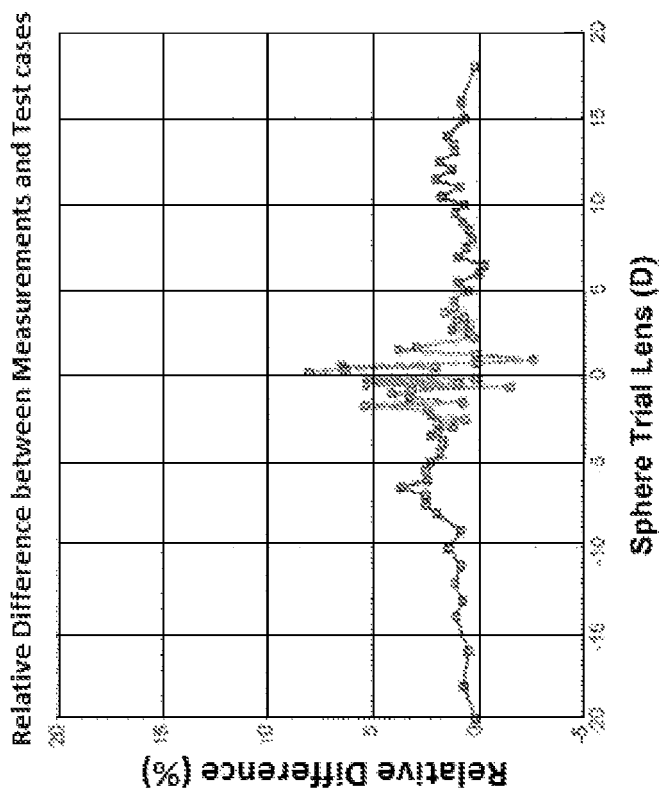
FIG. 26 shows the results of relative difference between measurements and test lenses for spherical test lenses from −20D to +18D (Mean relative error: 1.954%, Maximum excluding the gray masked data: 3.58%).
Figure 27:
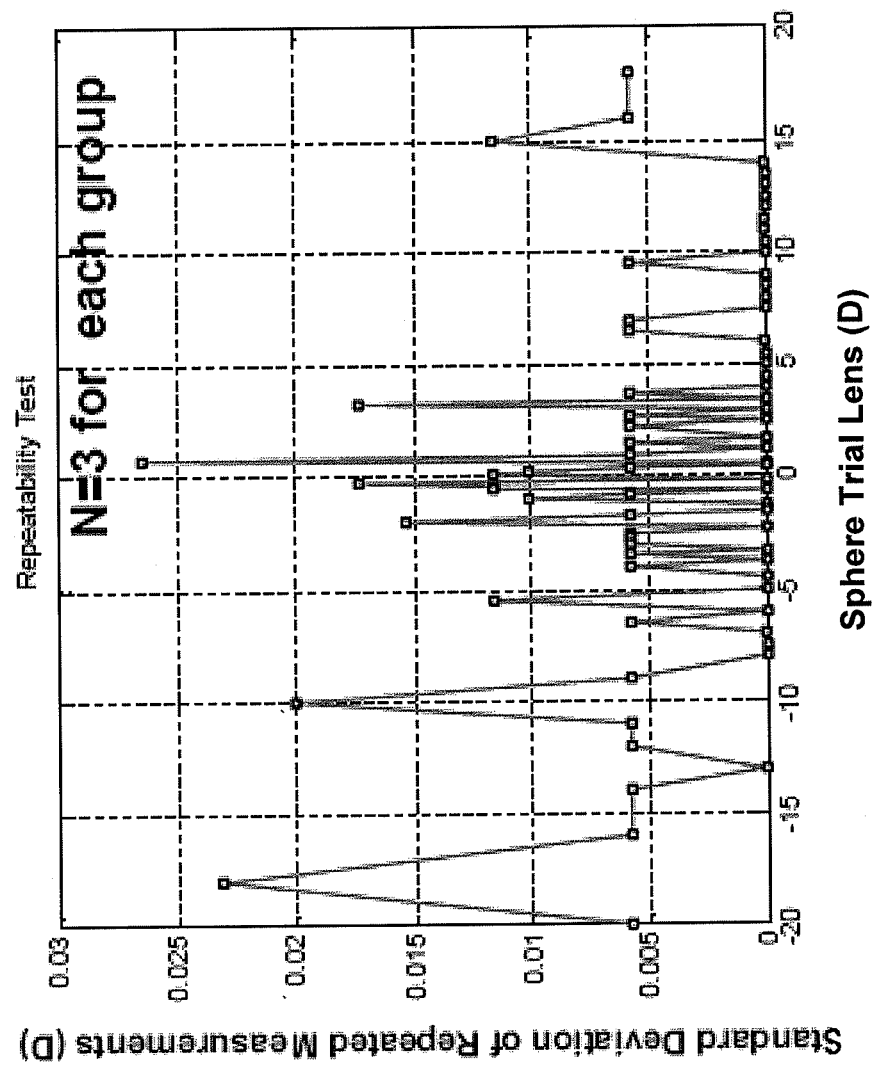
FIG. 27 shows the results of a repeatability test for spherical test lenses from −20D to +18D. Maximum deviation was less than 0.03D.
Figure 28:
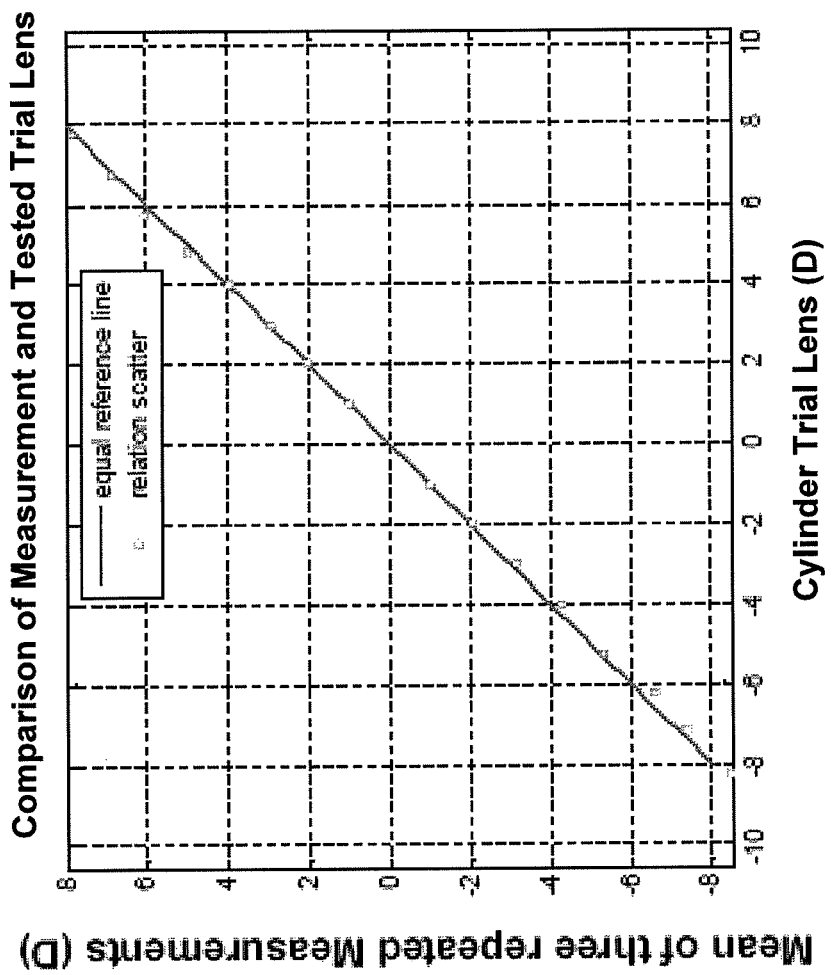
FIG. 28 shows the results of a comparison of measurement and tested trial lenses for cylindrical test lenses from −8D to +8D (correlation coefficient r=0.9999).
Figure 29:
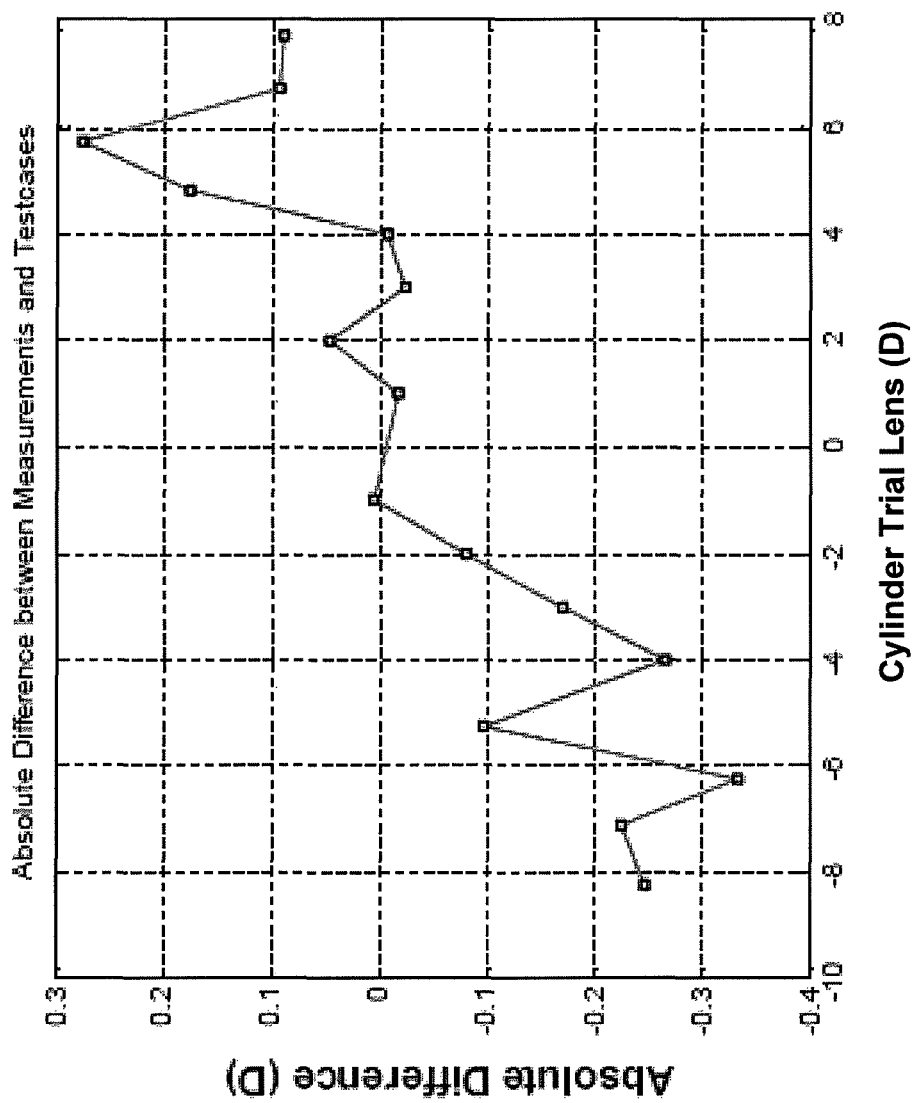
FIG. 29 shows the results of absolute difference between measurements and test lenses for cylindrical test lenses from −8D to +8D (Absolute mean difference: 0.1347D, Maximum difference: 0.33D).
Figure 30:
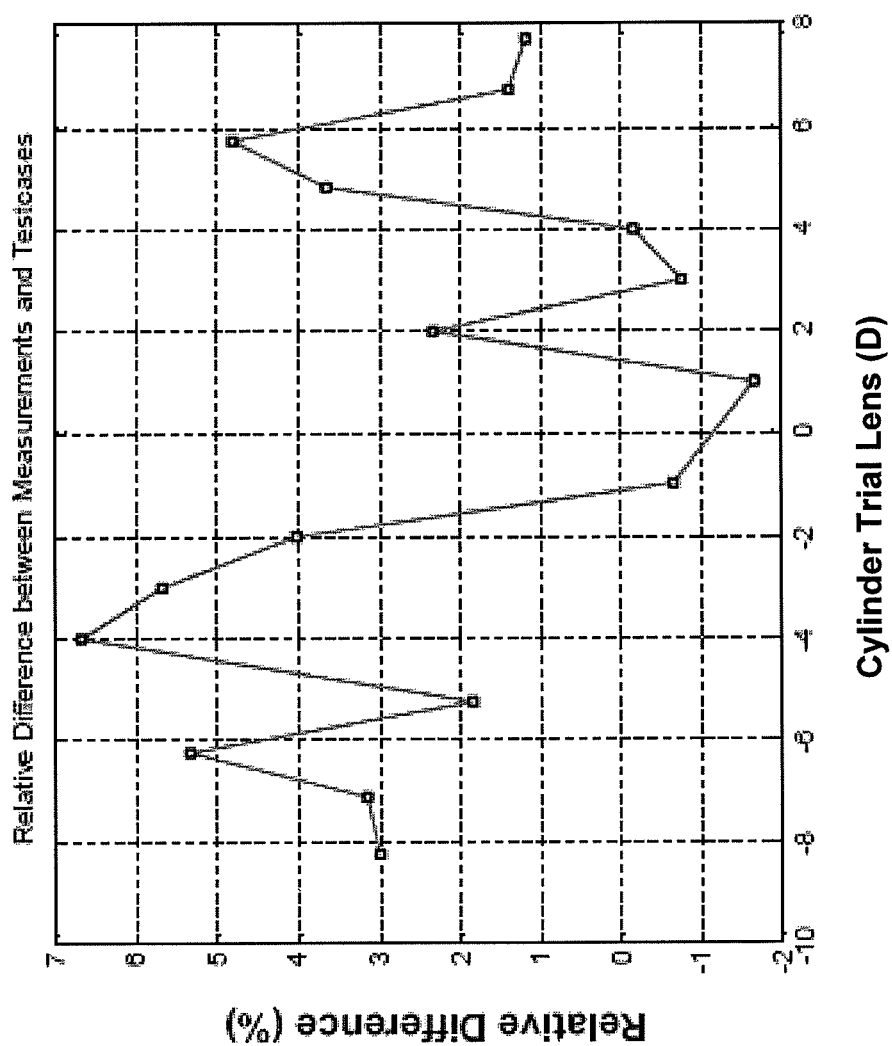
FIG. 30 shows the results of relative difference between measurements and test lenses for cylindrical test lenses from −8D to +8D (Mean relative error: 2.8925%).
Figure 31:
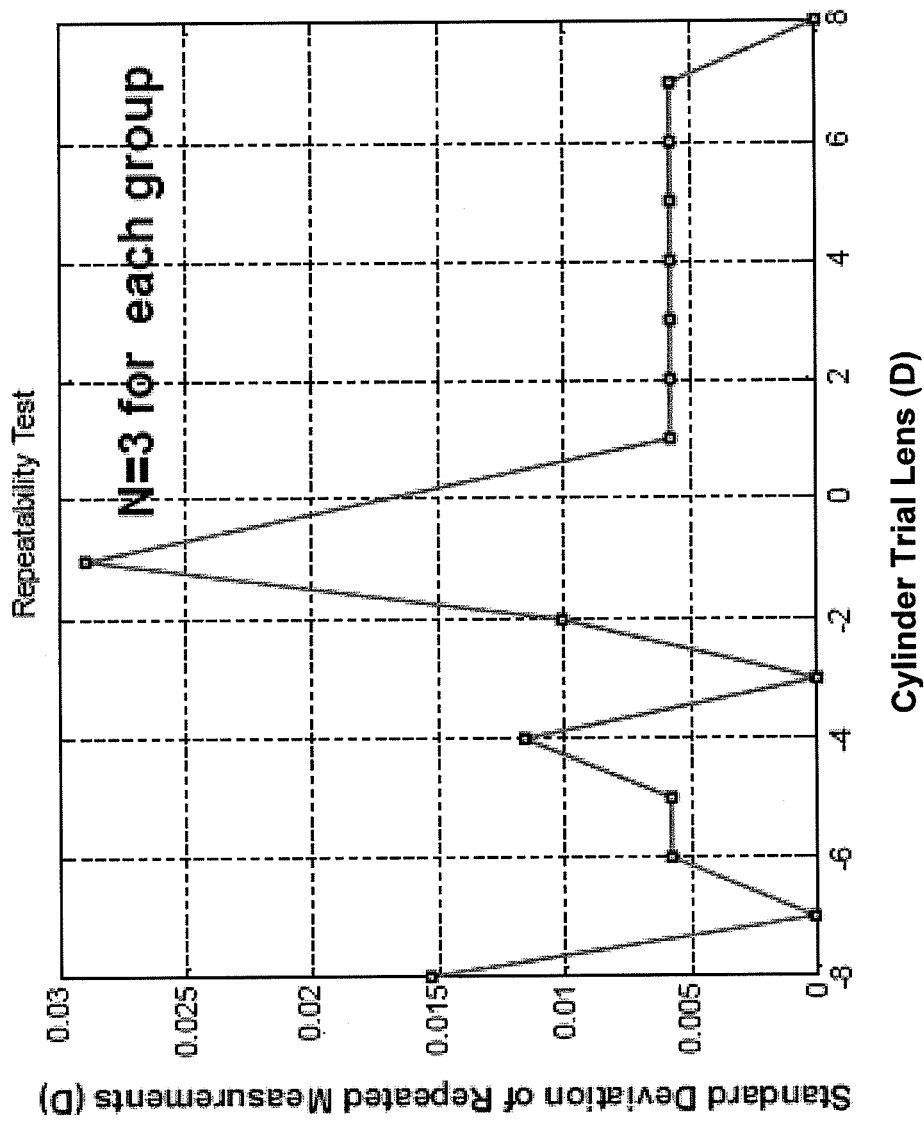
FIG. 31 shows the results of a repeatability test for cylindrical test lenses from −8D to +8D. Maximum deviation was less than 0.03D.

Measurements should be taken to assure tight alignment tolerance (decentration tilt). For example, for accuracy of 0.5D measured at −20D, the axial tolerance should be 1.28 mm. As shown in FIG. 23, the amount of measured cylinder was measured using a sphere lens from about −20D to +18D with fixed scheme (mean=0.04D, maximum=0.17D).

Defocus was accurately measured over a 38D range and astigmatism over a 16D range. Correlation coefficients between mean wavefront measurements (n=3) and expected refractions for both sphere and cylinder lenses were 1.00.

For spherical lenses, the instrument was accurate to within 0.2D over the range from −20D to +18D without any means to compensate refraction. Results for spherical test lenses are shown in FIGS. 24-27.

For cylindrical lenses, the instrument was accurate to within 0.15D over the range from −7D to +10D without any means to compensate refraction. The amplitude of measured astigmatism was accurate to within 0.33D within the range of 16D (−8D to +8D) without any means to compensate refraction. The amplitude of measured astigmatism was accurate to within 0.2D within the range of 11D (−3D to +5D) without any means to compensate refraction. Results for cylindrical test lenses are shown in FIGS. 28-31.

The repeatability for fixed condition measurements obtained within 2 minutes was within 0.03D. Improved accuracy would be expected after an optimized calibration that takes component tolerances into account.

These results demonstrate that the Hartmann-Moiré wavefront sensor measures defocus and astigmatism accurately and repeatedly over a large dynamic range of −20D to +18D for spherical lenses and over the range of −8D to 8D for cylindrical lenses.

EXAMPLE 2

Comparison of Hartmann-Moiré to Talbot-Moiré

Figure 32:
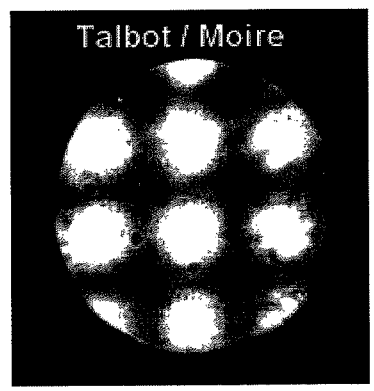
FIG. 32 shows a CCD camera photograph of the shadow patterns created by a comparative Talbot-Moiré wavefront sensor, wherein the two Talbot optics are configured to produce similar sized spot patterns as those depicted in the following Figure.
Figure 33:
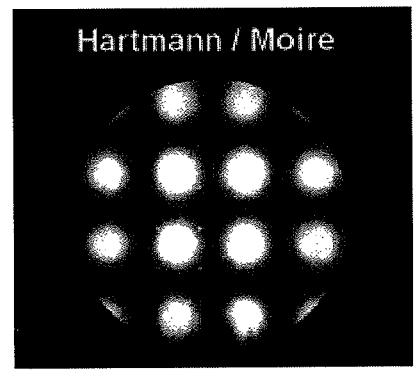
FIG. 33 shows a CCD camera photograph of the spot patterns created by a Hartmann-Moiré wavefront sensor configured to produce similar sized spot patterns as those depicted in the preceding Figure.
Figure 34:
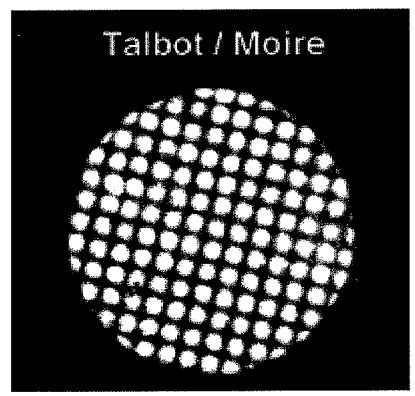
FIG. 34 shows a CCD camera photograph of the shadow patterns created by a comparative Talbot-Moiré wavefront sensor, wherein the two Talbot optics are configured to produce similar sized spot patterns as those depicted in the following Figure.
Figure 35:
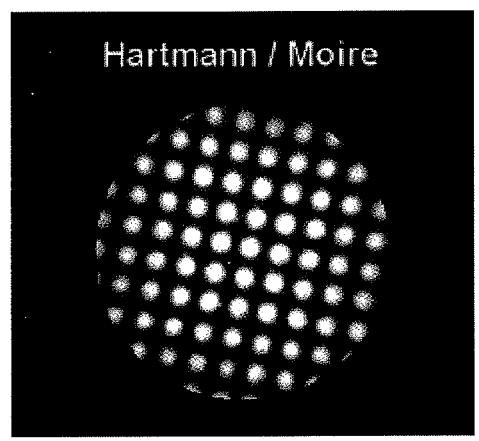
FIG. 35 shows a CCD camera photograph of the spot patterns created by a Hartmann-Moiré wavefront sensor configured to produce similar sized spot patterns as those depicted in the preceding Figure.

FIGS. 32-35 demonstrate the improved image quality achieved by the Hartmann-Moiré wavefront sensor described herein as compared with a Talbot-Moiré wavefront sensor. FIGS. 32 and 34 show CCD camera photographs of the shadow patterns created by a Talbot-Moiré wavefront sensor. FIGS. 33 and 35 show CCD camera photographs of the spot patterns created by a Hartmann-Moiré wavefront sensor configured to produce similar sized spots as the shadows depicted in FIGS. 32 and 34, respectively.

As shown by the comparative figures, the spots formed by the Hartmann-Moiré wavefront sensor are of a high image quality, allowing for a more accurate determination of each spot's center and a more accurate measurement of the spot's movement and position.

EXAMPLE 3

Comparative Examples for Measuring a Model Eye

Figure 36A:
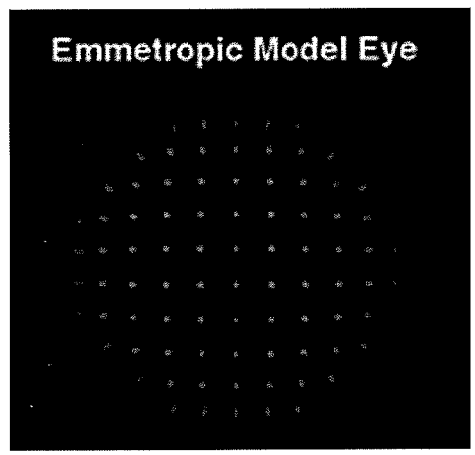
FIGS. 36A and B show images from a comparative Shack-Hartmann device.
Figure 36B:
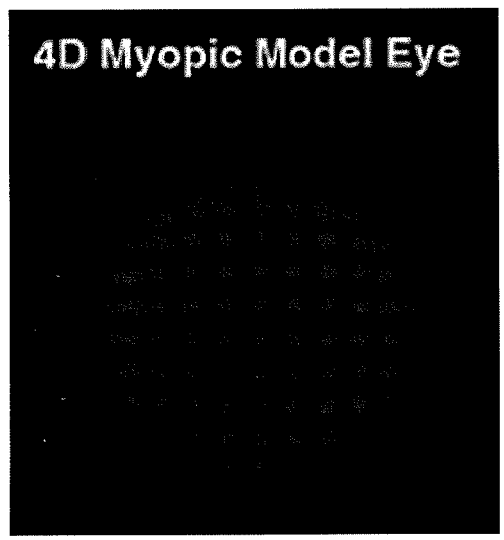
FIG. 36B shows a 4 Diopter eye.

FIG. 36 shows two images from a comparative Shack-Hartmann device. FIG. 36A shows spots of light formed when a plane wave is being measured (i.e., an emmetropic eye), and FIG. 36B shows spots of light formed when the model eye has a converging beam of light emerging from it (i.e., a myopic eye). As the beam of converging light passes through the Shack-Hartmann device, the spots grow closer together, and the amount that they have moved is easily observed. However, at the relatively low optical power of only four Diopters, the spots of light begin to lose their contrast and become blurry. This makes the task of determining the centroid of the spot of light difficult, if not impossible. As the power of the converging light grows beyond four Diopters, the spots of light will get even more blurry, to the point of where the device can no longer make a measurement, which is why this device has a low dynamic range.

Figure 37A:
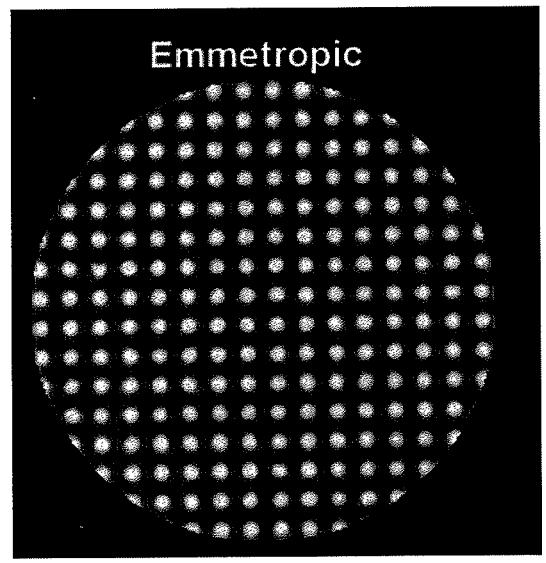
FIGS. 37A and B show two images from a comparative Hartmann Screen device.
Figure 37B:
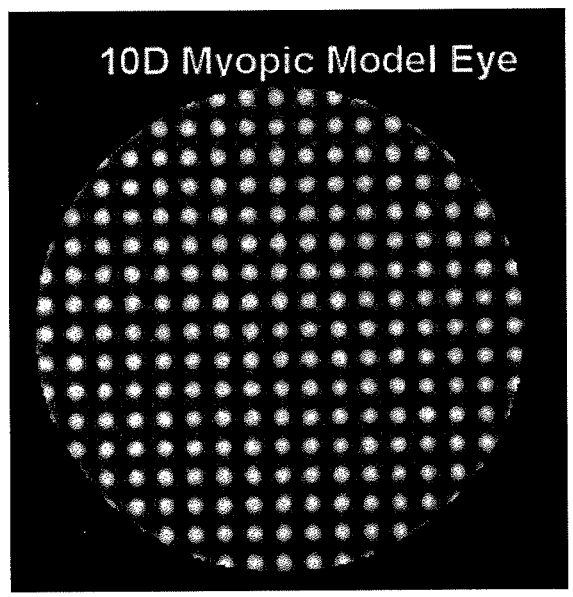
FIG. 37B shows a 10 Diopter eye.

FIG. 37 shows two images from a comparative Hartmann Screen device. FIG. 37A shows spots of light formed when a plane wave is being measured (i.e., an emmetropic eye), and FIG. 37B shows spots of light formed when the model eye has a converging beam of light emerging from it (i.e., a myopic eye). As the beam of converging light passes through the Hartmann device, the spots grow closer together, but the amount that they have moved is very small. Although at the relatively high optical power of ten Diopters the spots continue to have high contrast and are in sharp focus, the amount of movement of the spots is much smaller than the amount of movement of the spots in the Shack-Hartmann device, which is why this device has low sensitivity.

Figure 38A:
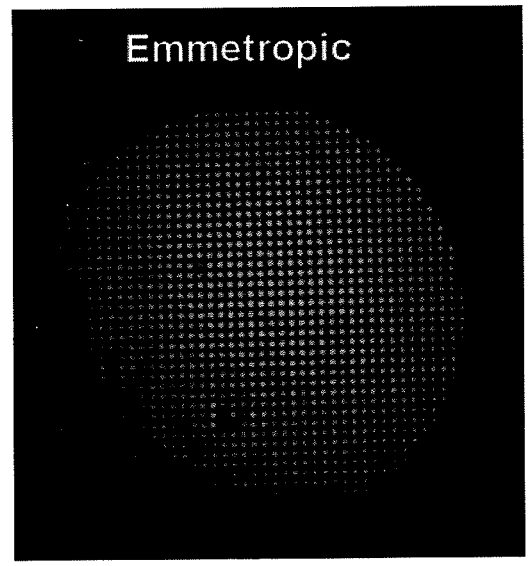
FIGS. 38A and B show two images from a Hartmann-Moiré device.
Figure 38B:
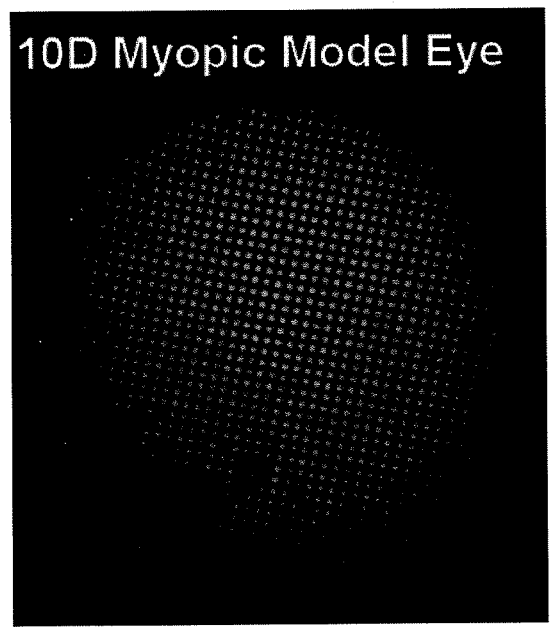
FIG. 38B shows a 10 Diopter eye.

FIG. 38 shows two images from a Hartmann-Moiré device as described herein. FIG. 38A shows spots of light formed when a plane wave is being measured (i.e., an emmetropic eye), and FIG. 38B shows spots of light formed when the model eye has a converging beam of light emerging from it (i.e., a myopic eye). As the beam of converging light passes through the Hartmann-Moiré device, the spots rotate clockwise, and the amount that they have moved is easily observed. Even at the relatively high optical power of ten Diopters the spots continue to have high contrast and are in sharp focus, which is why this device has both high sensitivity and a high dynamic range.

What is claimed is:

1. An apparatus comprising:
a light source emitting light along an optical axis;
a first screen comprising a first two-dimensional (2D) array of rounded apertures placed along the optical axis to receive the light from the light source;
a second screen comprising a second 2D array of rounded apertures placed along the optical axis to receive the light from the first screen, wherein the second screen is in a plane parallel to the first screen, and the second screen is rotated relative to the first screen about the optical axis so as to create a Moiré effect; and
a light detector placed to receive light from the second screen.

2. The apparatus of claim 1, wherein the first two-dimensional array and the second two-dimensional array are identical.

3. The apparatus of claim 1, wherein at least one of the first screen and the second screen is a Hartmann screen.

4. The apparatus of claim 3, wherein the first screen and the second screen are Hartmann screens.

5. The apparatus of claim 1, wherein at least one of the first screen and the second screen is a Shack-Hartmann lenslet array.

6. The apparatus of claim 5, wherein the first screen and the second screen are Shack-Hartmann lenslet arrays.

7. The apparatus of claim 1, wherein the second screen is rotated between 1 to 30 degrees about the optical axis relative to the first screen.

8. The apparatus of claim 1, further comprising a lens.

9. The apparatus of claim 8, wherein the lens is placed between the second screen and the light detector.

10. The apparatus of claim 8, wherein the lens is placed along the optical axis between the light source and the first screen.

11. The apparatus of claim 1, further comprising a beam splitter placed along the optical axis between the light source and the first screen.

12. A method of measuring characteristics of an eye comprising:
a) directing light into the eye;
b) directing the light from the eye through a first screen comprising a first two-dimensional array of rounded apertures;
c) directing the light from the first screen through a second screen comprising a second two-dimensional array of rounded apertures, wherein the second screen is placed downstream of the first screen, the second screen is in a plane parallel to the first screen, and the second screen is rotated relative to the first screen;

d) detecting focused spots of light from the second screen at a light detector.

13. The method of claim 12, wherein the first two-dimensional array and the second two-dimensional array are identical.

14. The method of claim 12, wherein at least one screen is a Hartmann screen.

15. The method of claim 14, wherein the first screen and the second screen are Hartmann screens.

16. The method of claim 12, wherein at least one screen is a Shack-Hartmann lenslet array.

17. The method of claim 16, wherein the first screen and the second screen are Shack-Hartmann lenslet arrays.

18. The method of claim 12, wherein the second screen is rotated about 1 to about 30 degrees relative to the first screen.

19. The method of claim 12, further comprising directing the light through a relay lens.

20. The method of claim 19, wherein the relay lens is placed between the second screen and the light detector.

* * * * *